US005698445A

United States Patent [19]

Abo et al.

[11] Patent Number: 5,698,445
[45] Date of Patent: Dec. 16, 1997

[54] HUMAN PAK65

[75] Inventors: Arie Abo, San Francisco; George A. Martin, Berkeley, both of Calif.

[73] Assignee: Onyx Pharmaceuticals, Inc., Richmond, Calif.

[*] Notice: The term of this patent shall not extend beyond the expiration date of Pat. No. 5,578,911.

[21] Appl. No.: 636,036

[22] Filed: Apr. 22, 1996

Related U.S. Application Data

[63] Continuation of Ser. No. 369,780, Jan. 6, 1995, Pat. No. 5,518,911.

[51] Int. Cl.$^6$ .............................. C12N 5/00; C12N 1/20; C12N 15/00; C07H 21/04
[52] U.S. Cl. ...................... 435/325; 435/348; 435/252.3; 435/320.1; 536/23.2
[58] Field of Search ..................... 536/23.2; 435/194, 435/325, 348, 252.3, 320.1

[56] References Cited

PUBLICATIONS

Nobes, C., and Hall, A. (1994) Curr. Opin. Gen. Devel. 4, 77–81.
Hart, M. J., Eva, A., Evans, T., Aaronson, S.A., Cerione, R.A. (1991) Nature 354, 311–314.
Boguski, M.S., McCormick, F. (1993) Nature, 366, 643–654.
Ridley, A.J., Hall, A. (1992) Cell 70, 389–399.
Ridley, A.J., Paterson, H.F., Johnston, C.L., Diekmann, D., Hall, A. (1992) Cell 70, 401–410.
Takaishi, K., Kikuchi, A., Kuroda, S., Kotani, K., Sasaki, T., Takai, Y. (1993), Mol. Cell. Biol. 13, 72–79.
Kishi, K., Sosaki T., Kuroda, S., Itah, T., Takai, Y. (1993) J. Cell. Biol. 120, 1187–95.
Tominaga, T., Sugie, K., Hirata M., Fukata, J., Uchida, A., Imura, H., Narumiya, S. (1993) J. Biol. Chem. 120, 1529–1537.
Johnson, D., Pringle, J. (1990) J. Cell Biol. 111, 143–152.
Gulbins, E., Coggeshall, K.M., Baier, G., Katzav, S., Burn, P., Altman, A. (1993) Science 260, 822–825.
Miki, T., Smith, C.L., Long, J.E., Eva, A., Flemming, T.P. (1993) Nature 362, 462–465.
Khosravi-Far, R., Chrzanowska-Wodnicka, M., Solski, P.A., Eva, A., Burridge, K., Der, C.J. (1994) Mol. Cell. Biol. 14, 6848–6857.
Abo, A., Pick, E., Hall, A., Totty, N., Teahan, C.G., Segal, A.W. (1991) Nature 353, 668–670.
Knaus, U. G., Heyworth, P.G., Evans, T., Curnutte, J.T., Bokoch, G..M. (1991) Science 254, 1512–1515.
Segal, A.W., Abo, A. (1993) Trends. Biochem. Sci. 18, 43–47.
Diekmann, D., Abo, A., Johnston, C., Segal, A.W., Hall, A. (1994) Science 265, 531–533.
Manser, E., Leung, T., Salihuddin, H., Zhao, Z., Lim, L. (1994) Nature 367, 40–46.
Zheng, Y., Bagrodia, S., Cerione, R.A. (1994) J. Biol. Chem. 269, 18727–18730.
Zhang, J., King, W.G., Dillon, S., Hall, A., Feig, L., Rittenhouse, S.E. (1993) J. Biol. Chem. 268, 22251–4.
Abo, A., Webb, M. R., Grogan, A., Segal, A.W. Biochem. J. (1994) 298, 585–591.
Kawasaki, H., and Suzuki, K., (1990) Anal. Biochem. 186, 264–268.
Totty, N.F., Waterfield, M.D. Hsuan, J.J. (1992) Prot. Sci. 1, 1215–1224.
Grussenmeyer, T., Scheidtmann, K.H., Hutchinson, M.A., Eckhart, W., Gernot, W. (1985) Proc. Natl. Acad. Sci. U.S.A. 82, 7952–7954.
Shacter, E. (1984) Anal. Biochem. 138, 416–420.
Cooper, A.J., Sefton, B.M., Hunter, T. (1983) in Methods in Enzymology 99, 37.
Manser, E., Leung, T., Monfries, C., Teo, M., Hall, C., Lim, L. (1992) J. Biol. Chem. 267, 16025–16028.
Ramer, S.W., and Davis, R.W. (1993) Proc. Nat. Acad. Sci. U.S.A. 90, 452–456.
Avruch, J., Zhang, X., Kyriakis, J. (1994) Trend. Biochem. Sci. 19, 279–284.
Leberer, E., Dignard, D., Harcus, D., Thomas, D.Y., Whiteway, M., (1992b) EMBO J. 11, 4805–4813.
Errede, B., Levin, D.E. (1993) Curr. Opin. Cell Biol. 5, 254–260.
Erree, B., Gartner, A., Zhou, Z., Nasmyth, K., Ammerer, G., (1993), Nature 362, 261–264.
Leberer, E., Dignard, D., Harcus, D., Hougan, L., Whiteway, M., Thomas, D.Y. (1993) Mol. Gen. Genet. 241, 241–254.
Settleman, J., Albright, C.F., Foster, L.C., Weinberg, R. A. (1992) Nature 359, 153–154.
Knaus et al., (1995) Science, 269, 221–223.
Benner et al. (1995) Activation of an SH6/H4 Kinase (PAK65) from Human Placenta by Intramolecular and Intermoleular Autophosphorylation J. Biol. Chem. 270(36): 21121–21128.

*Primary Examiner*—Robert A. Wax
*Assistant Examiner*—Lisa J. Hobbs
*Attorney, Agent, or Firm*—Nina M. Ashton; Gregory J. Giotta; Onyx Pharmaceuticals, Inc.

[57] ABSTRACT

A novel human serine protein kinase, human p21-protein activated serine kinase p65 protein, referred to as hPAK65, and methods for its preparation and use are provided. Nucleic acids encoding hPAK65 and methods for their use in preparing hPAK65 as well as in preparing and identifying hPAK65 analogs are provided. Methods provided for the use of hPAK65 protein and its protein fragments, such as those that retain at least one hPAK65 activity, that include screening libraries of agents for candidates that modulate hPAK65 activity. Methods are provided to identify agents that modulate the interaction of hPAK65 with rho-like p21 GTPases, particularly rac1 and CDC42Hs binding to hPAK65 and subsequent activation of hPAK65 serine protein kinase activity, that modulate hPAK65 serine protein kinase activity, and that modulate hPAK65 effect on p21 protein GTPase activity. Such modulating agents can provide novel chemotherapeutic agents for treatment of neoplasia, lymphoproliferative conditions, arthritis, inflammation, autoimmune diseases, apoptosis, and the like, that are related to hPAK65 and p21 protein signal transduction pathways.

15 Claims, 13 Drawing Sheets

```
          10         20         30         40
MSPILGYWKI KGLVQPTRLL LEYLEEKYEE HLYERDEGDK  40
WRNKKFELGL EFPNLPYYID GDVKLTQSMA IIRYIADKHN  80
MLGGCPKERA EISMLEGAVL DIRYGVSRIA YSKDFETLKV 120
DFLSKLPEML KMFEDRLCHK TYLNGDHVTH FDFMLYDALD 160
VVLYMDPMCL DAFPKLVCFK KRIEAIPQID KYLKSSKYIA 200

210        220        230        240
WPLQGWQATF GGGDHPPKSD LVPRGSKEKE RPEISPPSQF 240
EHTIHVGFDT VTGEFTGMPE QWARLLQTSN ITKLEQKKNP 280
QAVLDVLKFY D   291
```

FIG. 10

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2248 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
( B ) CLONE: hPAK65

( i x ) FEATURE:
( A ) NAME/KEY: CDS
( B ) LOCATION: 391..1908

( x i ) SEQUENCE DESCRIPTION: SEQ ID NO:1:

```
AGGGGAGGAC ACACTTCTGG CAAACGTTTC TCAAATCTGC TTCATCCAAT GTGAAGTTCA        60

TCTTGCAGCA TTTACTATGC ACAACAGAGT AACTATCGGG TCCTGTGGAC AGCTCACCTA       120

GTGGCAATGG CTCCAGGCTC CCGGACATCC CGTCTCCTGG CTTTTGCCTG CTCTGCCTGC       180

CCTGGCTTCA AGAGGCTGGT GCGTCCAAAC CGTTCCGTTA TCCAGGCTTT TTGACCACGC       240

TATGCTCCAA GCCCATGCGC GCACCAGCTG GCCATTGACA CCTACCAGGA GTTTGAAGAA       300

ACCTATATCC CAAAGGACCA GAAGTATTCA TTCCTGCATG ACTCCAGAC CTCCTTCTGC        360

TTCTCAGACT CTATTCCGAC ACCCTCCAAC ATG GAG GAA ACG CAA CAG AAA TCC       414
                                  Met Glu Glu Thr Gln Gln Lys Ser
                                   1               5

AAT CTA GAG CTG CTG TCA GCC AAT CAC AGT TTG AAA CCT TTG CCC TCT        462
Asn Leu Glu Leu Leu Ser Ala Asn His Ser Leu Lys Pro Leu Pro Ser
         10                  15                  20

GTT CCA GAA GAG AAA AAG CCC AGG CAT AAA ATC ATC TCC ATA TTC TCA        510
Val Pro Glu Glu Lys Lys Pro Arg His Lys Ile Ile Ser Ile Phe Ser
 25                  30                  35                  40

GGC ACA GAG AAA GGA AGT AAA AAG AAA GAA AAG GAA CGG CCA GAA ATT        558
Gly Thr Glu Lys Gly Ser Lys Lys Lys Glu Lys Glu Arg Pro Glu Ile
             45                  50                  55

TCT CCT CCA TCT GAT TTT GAG CAC ACC ATC CAT GTT GGC TTT GAT ACT        606
Ser Pro Pro Ser Asp Phe Glu His Thr Ile His Val Gly Phe Asp Thr
                 60                  65                  70

GTT ACT GGA GAA TTC ACT GGC ATG CCA GAA CAG TGG GCT CGA TTA CTA        654
Val Thr Gly Glu Phe Thr Gly Met Pro Glu Gln Trp Ala Arg Leu Leu
             75                  80                  85

CAG ACC TCC AAT ATC ACC AAA CTA GAG CAA AAG AAG AAT CCT CAG GCT        702
Gln Thr Ser Asn Ile Thr Lys Leu Glu Gln Lys Lys Asn Pro Gln Ala
         90                  95                 100

GTG CTG GAT GTC CTA AAG TTC TAC GAC TCC AAC ACA GTG AAG CAG AAA        750
Val Leu Asp Val Leu Lys Phe Tyr Asp Ser Asn Thr Val Lys Gln Lys
105                 110                 115                 120

TAT CTG AGC TTT ACT CCT CCT GAG AAA GAT GGC TTT CCT TCT GGA ACA        798
Tyr Leu Ser Phe Thr Pro Pro Glu Lys Asp Gly Phe Pro Ser Gly Thr
                125                 130                 135

CCA GCA CTG AAT GCC AAG GGA ACA GAA GCA CCC GCA GTA GTG ACA GAG        846
```

```
          Pro  Ala  Leu  Asn  Ala  Lys  Gly  Thr  Glu  Ala  Pro  Ala  Val  Val  Thr  Glu
                         140                     145                     150

GAG  GAG  GAT  GAT  GAT  GAA  GAG  ACT  GCT  CCT  CCC  GTT  ATT  GCC  CCG  CGA              894
Glu  Glu  Asp  Asp  Asp  Glu  Glu  Thr  Ala  Pro  Pro  Val  Ile  Ala  Pro  Arg
          155                     160                     165

CCG  GAT  CAT  ACA  AAA  TCA  ATT  TAC  ACA  CGG  TCT  GTA  ATT  GAC  CCT  GTT              942
Pro  Asp  His  Thr  Lys  Ser  Ile  Tyr  Thr  Arg  Ser  Val  Ile  Asp  Pro  Val
          170                     175                     180

CCT  GCA  CCA  GTT  GGT  GAT  TCA  CAT  GTT  GAT  GGT  GCT  GCC  AAG  TCT  TTA              990
Pro  Ala  Pro  Val  Gly  Asp  Ser  His  Val  Asp  Gly  Ala  Ala  Lys  Ser  Leu
185                     190                     195                     200

GAC  AAA  CAG  AAA  AAG  AAG  ACT  AAG  ATG  ACA  GAT  GAA  GAG  ATT  ATG  GAG             1038
Asp  Lys  Gln  Lys  Lys  Lys  Thr  Lys  Met  Thr  Asp  Glu  Glu  Ile  Met  Glu
               205                     210                     215

AAA  TTA  AGA  ACT  ATC  GTG  AGC  ATA  GGT  GAC  CCT  AAG  AAA  AAA  TAT  ACA             1086
Lys  Leu  Arg  Thr  Ile  Val  Ser  Ile  Gly  Asp  Pro  Lys  Lys  Lys  Tyr  Thr
               220                     225                     230

AGA  TAT  GAA  AAA  ATT  GGA  CAA  GGG  GCT  TCT  GGT  ACA  GTT  TTC  ACT  GCT             1134
Arg  Tyr  Glu  Lys  Ile  Gly  Gln  Gly  Ala  Ser  Gly  Thr  Val  Phe  Thr  Ala
          235                     240                     245

ACT  GAC  GTT  GCA  CTG  GGA  CAG  GAG  GTT  GCT  ATC  AAA  CAA  ATT  AAT  TTA             1182
Thr  Asp  Val  Ala  Leu  Gly  Gln  Glu  Val  Ala  Ile  Lys  Gln  Ile  Asn  Leu
          250                     255                     260

CAG  AAA  CAG  CCA  AAG  AAG  GAA  CTG  ATC  ATT  AAC  GAG  ATT  CTG  GTG  ATG             1230
Gln  Lys  Gln  Pro  Lys  Lys  Glu  Leu  Ile  Ile  Asn  Glu  Ile  Leu  Val  Met
265                     270                     275                     280

AAA  GAA  TTG  AAA  AAT  CCC  AAC  ATC  GTT  AAC  TTT  TTG  GAC  AGT  TAC  CTG             1278
Lys  Glu  Leu  Lys  Asn  Pro  Asn  Ile  Val  Asn  Phe  Leu  Asp  Ser  Tyr  Leu
               285                     290                     295

GTA  GGA  GAT  GAA  TTG  TTT  GTG  GTC  ATG  GAA  TAC  CTT  GCT  GGG  AGG  TCA             1326
Val  Gly  Asp  Glu  Leu  Phe  Val  Val  Met  Glu  Tyr  Leu  Ala  Gly  Arg  Ser
               300                     305                     310

CTC  ACT  GAT  GTG  GTA  ACA  GAA  ACG  TGC  ATG  GAT  GAA  GCA  CAG  ATT  GCT             1374
Leu  Thr  Asp  Val  Val  Thr  Glu  Thr  Cys  Met  Asp  Glu  Ala  Gln  Ile  Ala
          315                     320                     325

GCT  GTA  TGC  AGA  GAG  TGT  TTA  CAG  GCA  TTG  GAG  TTT  TTA  CAT  GCT  AAT             1422
Ala  Val  Cys  Arg  Glu  Cys  Leu  Gln  Ala  Leu  Glu  Phe  Leu  His  Ala  Asn
330                     335                     340

CAA  GTG  ATC  CAC  AGA  GAC  ATC  AAA  AGT  GAC  AAT  GTA  CTT  TTG  GGA  ATG             1470
Gln  Val  Ile  His  Arg  Asp  Ile  Lys  Ser  Asp  Asn  Val  Leu  Leu  Gly  Met
345                     350                     355                     360

GAA  GGA  TCT  GTT  AAG  CTC  ACT  GAC  TTT  GGT  TTC  TGT  GCC  CAG  ATC  ACC             1518
Glu  Gly  Ser  Val  Lys  Leu  Thr  Asp  Phe  Gly  Phe  Cys  Ala  Gln  Ile  Thr
               365                     370                     375

CCT  GAG  CAG  AGC  AAA  CGC  AGT  ACC  ATG  GTC  GGA  ACG  CCA  TAC  TGG  ATG             1566
Pro  Glu  Gln  Ser  Lys  Arg  Ser  Thr  Met  Val  Gly  Thr  Pro  Tyr  Trp  Met
               380                     385                     390

GCA  CCA  GAG  GTG  GTT  ACA  CGG  AAA  GCT  TAT  GGC  CCT  AAA  GTC  GAC  ATA             1614
Ala  Pro  Glu  Val  Val  Thr  Arg  Lys  Ala  Tyr  Gly  Pro  Lys  Val  Asp  Ile
          395                     400                     405

TGG  TCT  CTG  GGT  ATC  ATG  GCT  ATT  GAG  ATG  GTA  GAA  GGA  GAG  CCT  CCA             1662
Trp  Ser  Leu  Gly  Ile  Met  Ala  Ile  Glu  Met  Val  Glu  Gly  Glu  Pro  Pro
          410                     415                     420

TAC  CTC  AAT  GAA  AAT  CCC  CTT  AGG  GCC  TTG  TAC  CTA  ATA  GCA  ACT  AAT             1710
Tyr  Leu  Asn  Glu  Asn  Pro  Leu  Arg  Ala  Leu  Tyr  Leu  Ile  Ala  Thr  Asn
425                     430                     435                     440

GGA  ACC  CCA  GAA  CTT  CAG  AAT  CCA  GAG  AAA  CTT  TCC  CCA  ATA  TTT  CGG             1758
Gly  Thr  Pro  Glu  Leu  Gln  Asn  Pro  Glu  Lys  Leu  Ser  Pro  Ile  Phe  Arg
               445                     450                     455

GAT  TTC  TTA  AAT  CGA  TGT  TTG  GAA  ATG  GAT  GTG  GAA  AAA  AGG  GGT  TCA             1806
```

-continued

```
        Asp Phe Leu Asn Arg Cys Leu Glu Met Asp Val Glu Lys Arg Gly Ser
                        460                 465                 470

GCC AAA GAA TTA TTA CAG CAT CCT TTC CTG AAA CTG GCC AAA CCG TTA              1854
Ala Lys Glu Leu Leu Gln His Pro Phe Leu Lys Leu Ala Lys Pro Leu
            475                 480                 485

TCT AGC TTG ACA CCA CTG ATC ATG GCA GCT AAA GAA GCA ATG AAG AGT              1902
Ser Ser Leu Thr Pro Leu Ile Met Ala Ala Lys Glu Ala Met Lys Ser
        490                 495                 500

AAC CGT TAACATCACT GCTGTGGCCT CATACTCTTT TTTCCATTTT CTACAAGAAG               1958
Asn Arg
505

CCTTTTAGTA TATGAAAATT ATTACTCTTT TTGGGGTTTA AAGAAATGGT CTGCATAACC            2018

TGAATGAAAG AAGCAAATGA CTATTCTCTG AAGACAACCA AGAGAAAATT GCAAAAGAC             2078

AAGTATGACT TTTATATGAA CCCCTTCTTT AGGGTCCAGA AGGAATTGTG GACTGAATCA            2138

CTAGCCTTAG GTCTTTCAGC AAACAGCCTA TCAGGGCCAT TTATCATGTG TGAGATTTGC            2198

ATTTTACTTT GCTGACTTTG TTGTAATAGA TCCCATTCAT TGTCCCCTTT                       2248
```

( 2 ) INFORMATION FOR SEQ ID NO:2:

( i ) SEQUENCE CHARACTERISTICS:
        ( A ) LENGTH: 506 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Glu Thr Gln Gln Lys Ser Asn Leu Glu Leu Leu Ser Ala Asn
 1               5                  10                  15

His Ser Leu Lys Pro Leu Pro Ser Val Pro Glu Glu Lys Lys Pro Arg
            20                  25                  30

His Lys Ile Ile Ser Ile Phe Ser Gly Thr Glu Lys Gly Ser Lys Lys
        35                  40                  45

Lys Glu Lys Glu Arg Pro Glu Ile Ser Pro Pro Ser Asp Phe Glu His
    50                  55                  60

Thr Ile His Val Gly Phe Asp Thr Val Thr Gly Glu Phe Thr Gly Met
65                  70                  75                  80

Pro Glu Gln Trp Ala Arg Leu Leu Gln Thr Ser Asn Ile Thr Lys Leu
                85                  90                  95

Glu Gln Lys Lys Asn Pro Gln Ala Val Leu Asp Val Leu Lys Phe Tyr
            100                 105                 110

Asp Ser Asn Thr Val Lys Gln Lys Tyr Leu Ser Phe Thr Pro Pro Glu
        115                 120                 125

Lys Asp Gly Phe Pro Ser Gly Thr Pro Ala Leu Asn Ala Lys Gly Thr
    130                 135                 140

Glu Ala Pro Ala Val Val Thr Glu Glu Glu Asp Asp Glu Glu Thr
145                 150                 155                 160

Ala Pro Pro Val Ile Ala Pro Arg Pro Asp His Thr Lys Ser Ile Tyr
                165                 170                 175

Thr Arg Ser Val Ile Asp Pro Val Pro Ala Pro Val Gly Asp Ser His
            180                 185                 190

Val Asp Gly Ala Ala Lys Ser Leu Asp Lys Gln Lys Lys Lys Thr Lys
        195                 200                 205

Met Thr Asp Glu Glu Ile Met Glu Lys Leu Arg Thr Ile Val Ser Ile
    210                 215                 220

Gly Asp Pro Lys Lys Lys Tyr Thr Arg Tyr Glu Lys Ile Gly Gln Gly
```

| 225 | | | | 230 | | | | 235 | | | | 240 | |
|---|---|---|---|---|---|---|---|---|---|---|---|---|---|
| Ala | Ser | Gly | Thr | Val 245 | Phe | Thr | Ala | Thr | Asp 250 | Val | Ala | Leu | Gly | Gln 255 | Glu |
| Val | Ala | Ile | Lys 260 | Gln | Ile | Asn | Leu | Gln 265 | Lys | Gln | Pro | Lys | Lys 270 | Glu | Leu |
| Ile | Ile | Asn 275 | Glu | Ile | Leu | Val | Met 280 | Lys | Glu | Leu | Lys | Asn 285 | Pro | Asn | Ile |
| Val | Asn 290 | Phe | Leu | Asp | Ser | Tyr 295 | Leu | Val | Gly | Asp | Glu 300 | Leu | Phe | Val | Val |
| Met 305 | Glu | Tyr | Leu | Ala | Gly 310 | Arg | Ser | Leu | Thr | Asp 315 | Val | Val | Thr | Glu | Thr 320 |
| Cys | Met | Asp | Glu | Ala 325 | Gln | Ile | Ala | Ala | Val 330 | Cys | Arg | Glu | Cys | Leu 335 | Gln |
| Ala | Leu | Glu | Phe 340 | Leu | His | Ala | Asn | Gln 345 | Val | Ile | His | Arg | Asp 350 | Ile | Lys |
| Ser | Asp | Asn 355 | Val | Leu | Leu | Gly | Met 360 | Glu | Gly | Ser | Val | Lys 365 | Leu | Thr | Asp |
| Phe | Gly 370 | Phe | Cys | Ala | Gln | Ile 375 | Thr | Pro | Glu | Gln | Ser 380 | Lys | Arg | Ser | Thr |
| Met 385 | Val | Gly | Thr | Pro | Tyr 390 | Trp | Met | Ala | Pro | Glu 395 | Val | Val | Thr | Arg | Lys 400 |
| Ala | Tyr | Gly | Pro | Lys 405 | Val | Asp | Ile | Trp | Ser 410 | Leu | Gly | Ile | Met | Ala 415 | Ile |
| Glu | Met | Val | Glu 420 | Gly | Glu | Pro | Pro | Tyr 425 | Leu | Asn | Glu | Asn | Pro 430 | Leu | Arg |
| Ala | Leu | Tyr 435 | Leu | Ile | Ala | Thr | Asn 440 | Gly | Thr | Pro | Glu | Leu 445 | Gln | Asn | Pro |
| Glu | Lys 450 | Leu | Ser | Pro | Ile | Phe 455 | Arg | Asp | Phe | Leu | Asn 460 | Arg | Cys | Leu | Glu |
| Met 465 | Asp | Val | Glu | Lys | Arg 470 | Gly | Ser | Ala | Lys | Glu 475 | Leu | Leu | Gln | His | Pro 480 |
| Phe | Leu | Lys | Leu | Ala 485 | Lys | Pro | Leu | Ser | Ser 490 | Leu | Thr | Pro | Leu | Ile 495 | Met |
| Ala | Ala | Lys | Glu 500 | Ala | Met | Lys | Ser | Asn 505 | Arg | | | | | | |

HUMAN PAK65

CROSS REFERENCE TO RELATED APPLICATIONS

This application is a continuation of U.S. application Ser. No. 08/369,780, filed Jan. 6, 1995 now U.S. Pat. No. 5,518,911.

TECHNICAL FIELD

This invention relates to methods for making and using and compositions containing human p21-activated kinase p65 ("hPAK65") nucleic acid or protein sequences.

BACKGROUND

The rho-like proteins (i.e., p21 proteins), like other GTPases, cycle between an active GTP-bound form and an inactive GDP-bound state (Nobes and Hall, 1994). Regulation of these forms was shown to be controlled by several proteins including guanine nucleotide exchange factors ("GEF") such as Dbl and GTPase activating proteins (Hart et al. 1991, Boguski and McCormick, 1993). Members of the rho family of proteins, including RhoA, B, C, rac1, 2, CDC42Hs ("CDC42 Homo sapien"), and TC10, share at least 50% sequence identity with each other and 30% identity with other ras-like proteins (Nobes and Hall, 1994). Insight into the physiological function of rho and rac proteins emerged from recent reports described by Ridley and Hall (Ridley and Hall, 1992; Ridley et al., 1992), in which rapid cytoskeletal effects were detected when rho and rac proteins were micro injected into Swiss 3T3 fibroblasts. Activated rho induces stress fiber formation and focal contact (Ridley and Hall 1992) whereas activated rac induces the formation of membrane ruffles and lamelipodia (Ridley et al. 1992). Rho proteins are also implicated in other physiological roles associated with cytoskeletal rearrangements such as cell motility (Takaishi et al. 1993), cytokinesis (Kishi et al. 1993) and lymphocyte aggregation (Tominaga et al 1993).

Although the physiological function of CDC42 was shown to be essential in bud formation in yeast (Johnson and Pringle 1990), no similar physiological function was described for its mammalian homologue CDC42Hs. However, a hint for its role in mammalian cells came from a study demonstrating that the protooncogene Dbl exhibits GEF activity on rho and CDC42Hs (Hart et al. 1991). This observation suggests a role for rho-like proteins in cell transformation to a neoplatic state. However, not all proteins containing the Dbl domain demonstrate nucleotide exchange activity on rho-like proteins. For example, vav (Gulbins et al. 1993), Ect2 (Miki et al. 1993), ras GRF and bcr (Boguski and McCormick 1993) do not exert nucleotide exchange activity on rho, and the Dbl domain of bcr and ras GRF do not transform cells. A recent study suggests a direct link for rho and Dbl in vivo by demonstrating that vav and Dbl transformation is mediated by rho (Khosravi-Far et al. 1994).

p21 proteins are known to be integral components of signal transduction mechanisms leading to control of cell proliferation. Many pathological conditions result, at least in part, from aberrant control of cell proliferation or differentiation. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

Currently only a few effector molecules for rho-like proteins are known including rat brain kinase PAK65 (Manser et al. 1994) and p67-phox of NADPH oxidase (Diekmann et al 1994). From molecular function studies in phagocytes, it was demonstrated that rac 1 and 2 are involved in the control of superoxide generation by the NADPH oxidase (Abo et al. 1991, Knaus et al. 1991). Activated rac together with two other oxidase cytosolic components, p47-phox and p67-phox, assemble with the membrane bound cytochrome $b_{558}$ to form an active oxidase (Segal and Abo 1993). The effector molecule for rac in this system is p67-phox (Diekmann et al. 1994). An additional molecular effector for rac and CDC42Hs was shown to be a rat brain serine/threonine kinase, which is activated by rac1 and CDC42Hs (Manser et al. 1994). Other studies suggested that CDC42Hs and rho also can activate PI3 kinase (Zhang et al. 1993; Zheng et al. 1994).

In view of the potential and varied roles for rho-like p21 proteins in physiological pathways and disease states, such as cell structural integrity, physiological roles associated with cytoskeletal rearrangements such as cell motility, cytokinesis, lymphocyte aggregation, tumor cell transformation and proliferation, metasteses, cell aggregation, and the paucity of understanding of the molecules and agents that selectively effect or modulate the activities of these proteins in one or more of these physiological pathways, there thus exists a need in the art for compounds and agents with effector and modulator activity and methods to identify these and related compositions and agents. Further, such agents can serve as commercial research reagents for control of cell proliferation, differentiation, and other p21-related conditions. Despite progress in developing a more defined model of the molecular mechanisms underlying the transformed phenotype and neoplasia, few significant therapeutic methods applicable to treating cancer beyond conventional chemotherapy have resulted. Such p21 protein modulating agents can provide novel chemotherapeutic agents for treatment of neoplasia, lymphoproliferative conditions, arthritis, inflammation, autoimmune diseases, apoptosis, and the like. These and other objects are provided by this invention.

Relevant Literature

1. Nobes, C., and Hall, A. (1994) Curr. Opin. Gen. Devel. 4, 77–81.
2. Hart, M. J., Eva, A., Evans, T., Aaronson, S. A., Cerione, R. A. (1991) Nature 354, 311–314.
3. Boguski, M. S., McCormick, F. (1993) Nature, 366, 643–654.
4. Ridley, A. J., Hall, A. (1992) Cell 70, 389–399.
5. Ridley, A. J., Paterson, H. F., Johnston, C. L., Diekmann, D., Hall, A. (1992) Cell 70, 401–410.
6. Takaishi, K., Kikuchi, A., Kuroda, S., Kotani, K., Sasaki, T., Takai, Y. (1993), Mol. Cell. Biol. 13, 72–79.
7. Kishi, K., Sosaki, T., Kuroda, S., Itah, T., Takai, Y. (1993) J. Cell. Biol. 120, 1187–95.
8. Tominaga, T., Sugie, K., Hirata, M., Fukata, J., Uchida, A., Imura, H., Narumiya, S. (1993) J. Biol. Chem. 120, 1529–1537.
9. Johnson, D., Pringle, J. (1990) J. Cell Biol. 111, 143–152.
10. Gulbins, E., Coggeshall, K. M., Baier, G., Katzav, S., Burn, P., Altman, A. (1993) Science 260, 822–825.
11. Miki., T., Smith, C. L., Long, J. E., Eva, A., Flemming, T. P. (1993) Nature 362, 462–465.

12. Khosravi-Far, R., Chrzanowska-Wodnicka, M., Solski, P. A., Eva, A., Burridge, K., Der, C. J. (1994) Mol. Cell. Biol. 14, 6848–6857.
13. Abo, A., Pick, E., Hall, A., Totty, N., Teahan, C. G., Segal, A. W. (1991) Nature 353, 668–670.
14. Knaus, U. G., Heyworth, P. G., Evans, T., Curnutte, J. T., Bokoch, G. M. (1991) Science 254, 1512–1515.
15. Segal, A. W., Abo, A. (1993) Trends. Biochem. Sci. 18, 43–47.
16. Diekmann, D., Abo, A., Johnston, C., Segal, A. W., Hall, A. (1994) Science 265, 531–533.
17. Manser, E., Leung, T., Salihuddin, H., Zhao, Z., Lim, L. (1994) Nature 367, 40–46.
18. Zheng, Y., Bagrodia, S., Cerione, R. A. (1994) J. Biol. Chem. 269, 18727–18730.
19. Zhang, J., King, W. G., Dillon, S., Hall, A., Feig, L., Rittenhouse, S. E. (1993) J. Biol. Chem. 268, 22251–4.
20. Abo, A., Webb, M. R., Grogan, A., Segal, A. W. Biochem. J. (1994) 298, 585–591.
21. Kawasaki, H., and Suzuki, K., (1990) Anal. Biochem. 186, 264–268.
22. Totty, N. F., Waterfield, M. D., Hsuan, J. J. (1992) Prot. Sci. 1, 1215–1224.
23. Grussenmeyer, T., Scheidtmann, K. H., Hutchinson, M. A., Eckhart, W., Gernot, W. (1985) Proc. Natl. Acad. Sci. U.S.A. 82, 7952–7954.
24. Shacter, E. (1984) Anal. Biochem. 138, 416–420.
25. Cooper, A. J., Sefton, B. M., Hunter, T. (1983) in Methods in Enzymology 99, 37.
26. Manser, E., Leung, T., Monfries, C., Teo, M., Hall, C., Lim, L. (1992) J. Biol. Chem. 267, 16025–16028.
27. Ramier, S. W., and Davis, R. W. (1993) Proc. Nat. Acad. Sci. U.S.A. 90, 452–456.
28. Avruch, J., Zhang, X., Kyriakis, J. (1994) Trend. Biochem. Sci. 19, 279–284.
29. Leberer, E., Dignard, D., Harcus, D., Thomas, D. Y., Whiteway, M., (1992b) EMBO J. 11, 4805–4813.
30. Errede, B., Levin, D. E. (1993) Curr. Opin. Cell Biol. 5, 254–260.
31. Errede, B., Gartner, A., Zhou, Z., Nasmyth, K., Ammerer, G., (1993), Nature 362, 261–264.
32. Leberer, E., Dignard, D., Harcus, D., Hougan, L., Whiteway, M., Thomas, D. Y. (1993) Mol. Gen. Genet. 241, 241–254.
33. Settleman, J., Albright, C. F., Foster, L. C., Weinberg, R. A. (1992) Nature 359, 153–154.

SUMMARY OF THE INVENTION

The invention provides isolated polynucleotides comprising nucleic acid sequences encoding a novel human p21-protein activated serine kinase p65 protein ("hPAK65"). The invention provides isolated polynucleotides having nucleic acid sequences encoding hPAK65, preferably as described in FIG. 2A (SEQ ID NO:1), nucleic acid sequences complementary to that sequence, nucleic acid sequences containing degenerate codon replacements within the human PAK65 coding sequence of that sequence, allelic variants of that sequence, closely related variants having at least 95% homology to that sequence, and fragments at least 10 bases in length from those sequences and which will selectively hybridize to nucleic acids encoding hPAK65. The nucleic acids sequences are preferably those found in nature, although in view of this invention the polynucleotides containing these sequence can be prepared in numerous ways known in the art, including synthetic methods. Also provided are hPAK65 recombinant constructs, e.g. fusions, truncations, substitutions, that provide polypeptides having certain desirable properties such as constitutive serine kinase activity, p21 protein binding activity, and ease of purification and identification.

Also provided are isolated and purified hPAK65 proteins containing the sequneces found in the polynuclotides of the invention. Methods for preparation of hPAK65 proteins are provided, including isolation from natural sources, synthetic production, and recombinant production using the nucleic acid sequences provided by the invention. The invention provides a human hPAK65 protein, and fragments thereof, having an amino acid sequence depicted in FIG. 2A.

The invention includes vectors and transformed host cells for expressing the isolated polynucleotides of the invention when the isolated polynucleotides are operably linked to an expression vector appropriate for expression in the host cell used.

The isolated proteins of the invention having serine protein kinase activity are used to generate phosphorylated proteins and amino acids. Peptides of the invention can also be used to generate antibodies for detection assays and isolation methods of PAK65 and PAK65-complexes in PAK-65-related signal transduction pathways and disease conditions. The isolated polynucleotides the invention can find further use in the dissection of and in particular antisense treatments for PAK65-related signal transduction pathways and disease conditions.

The invention also provides compositions and methods to screen libraries of agents for their ability to modulate or inhibit the properties of hPAK65, which as disclosed herein include its protein kinase activity, its p21-protein binding activity, its p21-protein induced autophosphorylation activity, and its p21-bound phosphate release activity. Preferably the agents modulate the rac1- and CDC42Hs-interacting properties of human PAK65. The invention provides compositions and methods for treating or preventing neoplasia in human and veterinary patients, compositions and methods for screening a library of gents for pharmacological activity in regulating cell proliferation and/or cell differentiation, compositions and methods for modulation of a transformed cell phenotype in vitro, including use in bioprocess control and as commercial laboratory reagents. The present invention is also directed to pharmaceutical compositions for the control of hPAK65-dependent diseases in mammals which includes an agent capable of modulating at least one of the properties associated with hPAK65 and to a method of controlling hPAK65-dependent diseases which includes administering to a mammal suffering from a hPAK65 kinase dependent disease a hPAK65 kinase dependent disease controlling mount of an agent capable of modulating one of the properties associated with hPAK65. Mammal has the usual meaning and includes humans. Pharmaceutical uses are intended to include veterinary uses, especially use in domesticated animals such as cattle, sheep, pigs, goats, dogs, cats, rabbits, hamsters, gerbils, rats, and mice.

BRIEF DESCRIPTION OF THE DRAWINGS

FIG. 1B depicts a chromatogram showing fractionation of neutrophil cytosol on a Mono Q column, on which 10 ml (10 mg/ml) were applied and eluted with 30 ml of salt gradient. The collected fractions were analyzed by an overlay assay with [γ$^{32}$P]GTP CDC42Hs as a probe (FIG. 1A) as described in detail in the EXAMPLES section.

FIGS. 2A, 2B and 2C depict the nucleotide (SEQ ID NO:1) and deduced amino acid sequence (SEQ ID NO:2) of human PAK65 ("hPAK65"). hPAK65 cDNA was cloned from human placenta library. FIG. 2a presents a nucleic acid sequence of human PAK65 cDNA and its deduced amino acid sequence. In FIG. 2A the underlined amino acids correspond to the peptide sequence obtained from p65 purification. FIG. 2B depicts a comparison between the deduced amino acid sequences of hPAK65 and rat brain PAK65. FIG. 2C depicts a comparison between a putative kinase domain of hPAK65 and yeast STE20.

In FIG. 5A 1–2 ug of recombinant hPAK65 immobilized on beads in 40 µl kinase buffer, were incubated with 1–2 µg of the indicated GTPase which were preloaded with either GTP or GDP. The reaction was incubated for 20 min. at 30° C. with. 50 µM ATP and 5 µCi $[\gamma^{32}P]ATP$. Phosphorylated proteins were analyzed on SDS PAGE followed by an autoradiography. In FIG. 5B 4 µg of radio labeled phosphorylated hPAK65 mediated by CDC42Hs were hydrolyzed in 6N HCl, 110° C. for 2 hrs, and the phosphoamino acids were separated on a thin layer electrophoresis. $^{32}Pi$ labeled residues were detected by autoradiography. In FIG. 5C proteolytic digestion was performed with the indicated enzymes (trypsin, chymotrypsin, endoproteinase Glu-C) on hPAK65 which was either preincubated with rac1 or CDC42Hs in a kinase reaction containing $[\gamma^{32}P]ATP$. The radiolabeled peptides were resolved on a 16% Tricine gel and were visualized by autoradiography.

In FIG. 6A 3 µg of MBP were included with hPAK65 in a kinase reaction as described for FIG. 5A. In FIG. 6B 5 µl of the kinase reaction mixture was removed every 5 min and the reaction was stopped by adding SDS sample buffer. The phosphorylated MBP was separated on a 14% SDS PAGE, the band was excised, and the incorporated $^{32}Pi$ was counted. In FIG. 6C 4 µg of hPAK65 (30 µl beads) were first incubated for 20 min with 3 µg CDC42Hs in the presence (activated) or the absence (control) of ATP in a kinase reaction. To remove CDC42Hs, the hPAK65 beads were washed three times and hPAK65 was subjected to a second kinase reaction containing $[\gamma^{32}P]ATP$ and MBP. FIG. 6D presents hPAK65 kinase activity as counts per minute incorporated into MBP isolated from the blots of FIG. 6A.

FIG. 10 presents the amino acid sequence of the p21-binding fusion protein GST-PAKette.

DESCRIPTION OF SPECIFIC EMBODIMENTS

Figure 1A:
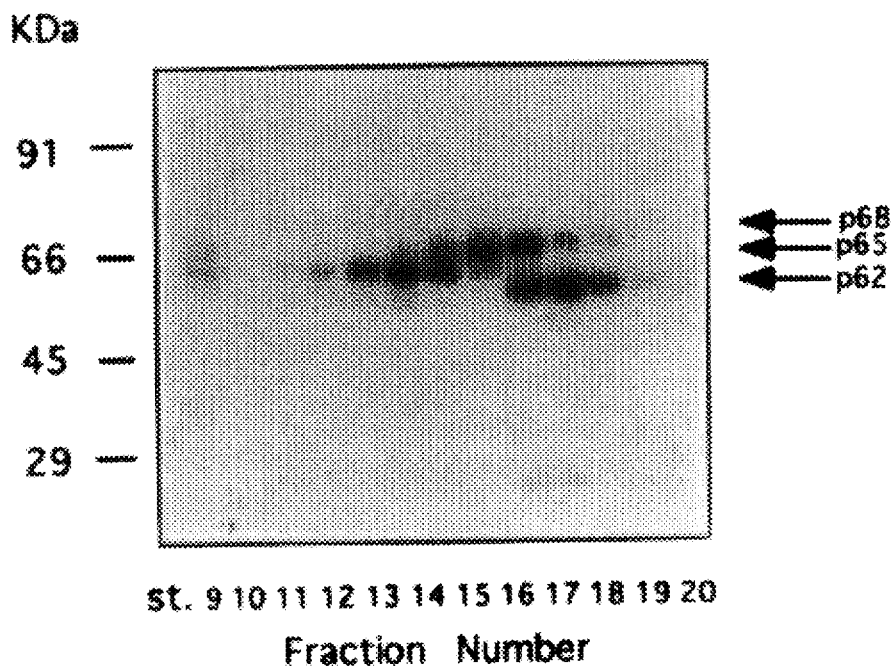
FIGS. 1A and 1B depict fractionation of neutrophil cytosol.

Novel compositions comprising isolated polynucleotides and oligonucleotides having nucleic acid sequences of hPAK65 are provided by the invention. Isolated proteins encoded by hPAK65 polynucleotides are also provided by the invention. Exemplary nucleic acid and amino acid sequences are set forth in SEQUENCE ID NO's 1 and 2, respectively. Aspects of the invention include isolated polynucleotides and oligonucleotides having nucleic acid sequences homologous to SEQUENCE ID NO:1 or encoding SEQUENCE ID NO:2; and isolated proteins having amino acid sequences homologous to SEQUENCE ID NO:2. Embodiments of the invention are achieved by either chemically synthesizing polynucleotides or oligonucleotides encoding hPAK65, in whole or in part, having at least 80% nucleic acid sequence homology (with preferably increasing homologies to 100%) to a human PAK65 nucleic acid sequence; or by isolating polynucleotides encoding a naturally occurring hPAK65 having at least 80% nucleic acid sequence homology (with preferably increasing homologies to 100%) to a nucleic acid sequence encoding human PAK65. For instance, techniques for synthesizing polynucleotides and oligonucleotides are well known in the art and changes can be made to the sequence of SEQUENCE ID NO:1 that allow for deviation from that sequence while permitting at least a 80% nucleic acid sequence homology to be maintained with the sequence described in SEQUENCE ID NO:1. In one preferred embodiment the sequences have at least 95% homology to the coding sequence of SEQUENCE ID NO 1.

Alternatively, in another embodiment of the invention polynucleotides encoding naturally occurring hPAK65 with at least 80% nucleic acid sequence homology to a human PAK65 nucleic acid sequence are isolated using isolated polynucleotides or oligonucleotides having nucleic acid sequences derived from SEQUENCE ID NO:1. Hybridization and wash conditions are known in the art, and discussed herein, that can be used to selectively hybridize probe nucleic acids generated from the sequence described in SEQUENCE ID NO:1 to nucleic acids with at least 80% nucleic acid sequence homology to human PAK nucleic acid sequence.

In the isolated protein aspects of the invention, isolated proteins of hPAK65 have amino acid sequences that correspond to a hPAK65 having at least 80% amino acid homology (with increasing preference for sequences with at least 85%, 90%, 95%, 99%, to having one amino acid difference) to a human PAK65 sequence, preferably to that of SEQUENCE ID NO 2. The isolated proteins of the invention can be expressed using the polynucleotides of the invention operably linked to an appropriate control sequence in an expression vector suitable for expression in either a mammalian, insect, yeast, or bacterial cell.

Definitions

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients. As employed throughout the disclosure, the following terms, unless otherwise indicated, shall be understood to have the following meanings:

The term "isolated polynucleotide" referred to herein means a polynucleotide of genomic, cDNA, or synthetic origin or some combination there of, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin the "isolated protein" (1) is not associated with proteins found in nature, (2) is free of other proteins from the same source, e.g. free of human proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred p21-interacting hPAK65 polypeptides include: the human full-length protein comprising the polypeptide sequence shown in FIG. 2A, polypeptides comprising a kinase domain, such as consisting essentially of a sequence shown in FIG. 2C, polypeptides comprising a p21-binding domain consisting essentially of amino acids 49 to 113 of FIG. 2A, polypeptides of hPAK65 missing amino acids 489, 490 and/or 491, or polypeptides of hPAK65 having amino acids corresponding to 380, 383 and/or 384 of FIG. 2A replaced with Glu or Asp.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "operably linked" referred to herein refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "control sequence" referred to herein refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence from hPAK65 that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

The term "selectively hybridize" referred to herein means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing such as a SEQUENCE ID NO 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the human PAK65 polynucleotide sequence shown in FIG. 2A.

As used herein, the twenty conventional amino acids and their abbreviations follow conventional usage (Immunology—A Synthesis, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstimted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethylysine, $\epsilon$-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is ysine, arginine, and histidine; and a group of amino acids having sulfur-containing side chains is cysteine and methionine. Preferred conservative amino acids substitution groups are: valine-leucine-isoleucine, phenylalaninetyrosine, lysine-arginine, alanine-valine, glutamic-aspartic, and asparagine-glutamine.

Figure 2A:
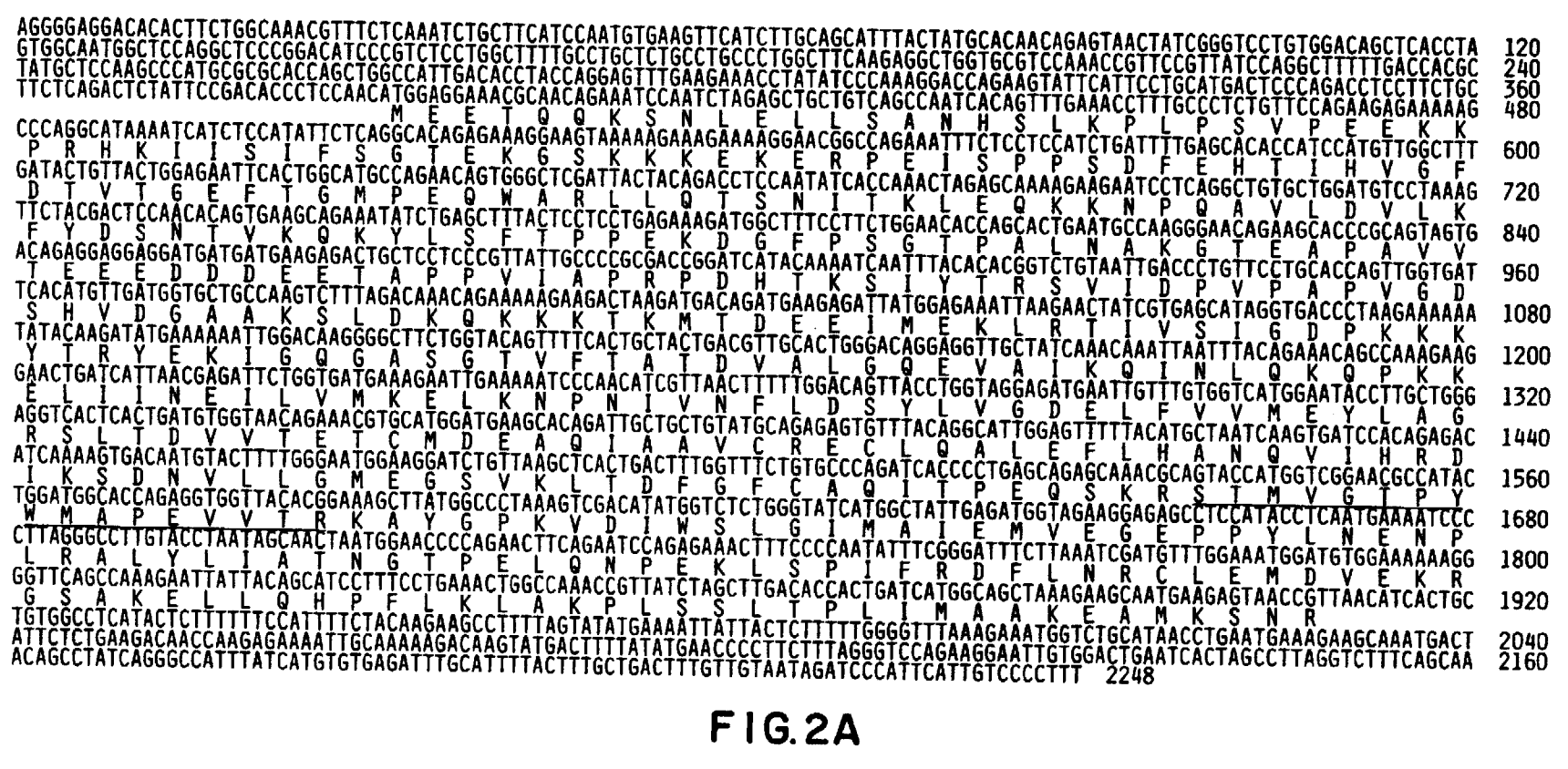

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence (e.g., the cDNA sequence shown in FIG. 2A). Fragments typically are at least 5, 6, 8 or 10 amino acids long, preferably at least 14 amino acids long, more preferably at least 20 amino acids long, usually at least 50 amino acids long, and even more preferably at least 70 amino acids long.

The term "analog" as used herein refers to polypeptides which are comprised of a segment of at least 25 amino acids that has substantial identity to a portion of the deduced amino acid sequence shown in FIG. 2A and which has at least one of the following properties: (1) specific binding to a p21 polypeptide, preferably rac1 or CDC42Hs, under suitable binding conditions, (2) ability to effectuate a p21 protein activity, preferably rac1 or CDC42Hs activity, when expressed in a mammalian cell, (3) serine protein kinase activity, or (4) ability to modulate p21 protein activity, preferably rac1 or CDC42Hs GTPase activity. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring hPAK65 polypeptide as shown in FIG. 2A. Some p21-interacting hPAK65 polypeptide analogs may lack biological activity but may still be employed for various uses, such as for raising antibodies to p21-interacting PAK polypeptide epitopes, as an immunological reagent to detect and/or purify p21-interacting PAK polypeptide antibodies by affinity chromatography, or as a competitive or noncompetitive agonist, antagonist, or partial agonist of native p21-interacting hPAK65 polypeptide function.

The term "modulation of human PAK65" is used herein to refer to the capacity to either enhance or inhibit a functional property of human PAK65 (e.g., kinase activity, p21-binding); such enhancement or inhibition may be contingent on the occurrence of a specific event, such as activation of a signal transduction pathway, and/or may be manifest only is particular cell types.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as human PAK65 modulatory agents (e.g., antineoplastic agents, cytotoxic agents, inhibitors of neoplastic transformation or cell proliferation, cell proliferation-promoting agents, Ras-induced tumorigenicity, and the like) by inclusion in screening assays described herein.

The term "candidate agent" is used herein to refer to an agent which is identified by one or more screening method (s) of the invention as a putative human PAK65 modulatory agent. Some candidate modulatory agents have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Detection of hPAK65 Nucleic Using hPAK65 Polynucleotides

The isolated polynucleotides of the invention can be used as probes to detect, and if desired to clone, PAK65 in a sample from an organism. The sample is typically from tissue. (Sambrook, J., Fritsch, E. F., and Maniatis, T., Molecular Cloning, second edition (1989) (referred to herein as "Sambrook et al.") Isolated polynucleotides with nucleic acid sequences encoding human PAK65 (e.g. SEQ ID NO:1) can be used as probes to detect the presence of target nucleic acid sequences with sequence homology. Polynucleotide probes are prepared and labelled by methods known in the art, e.g., Sambrook et al, especially chapter 10, the text of sections on preparing and labeling nucleic acids is herein incorporated by reference. For example, the polymerase chain reaction can be used to amplify the DNA and a biotin-avidin label system can be used to label and detect the target polynucleotide. Polynucleotide probes are hybridized with target nucleic acids at appropriate hybridization temperatures (e.g. see Sambrook et al; the text of Chapter 9 is herein incorporated by reference); and washed at low and high wash stringencies, depending on the detection assay.

Preferably polynucleotides are used as probes under high stringency wash conditions and with corresponding hybridization conditions, as known in the art. Isolated polynucleotides can be used to make probes that are 50 base pairs to the full length of hPAK65 cDNA. Preferably probes are made from isolated polynucleotides 100–400 nucleotides in length. Such conditions can be used to detect alleles of the hPAK65 gene in humans.

Alternatively, oligonucleotides can be employed as probes. Techniques for using oligonucleotides as probes to detect the same or related nucleic acid sequences is well known in the art, see for example Sambrook et al, especially Chapter 11, the text of which is herein incorporated by reference. Probes can be made from oligonucleotides that are 10 to 200 bases in length. Preferably probes are made from oligonucleotides 10 to 60 nucleotides in length and most preferably 12 to 40 bases in length. To decrease the number of false positives, preferably two probes are used to identify clones that bind to both probes under hybridization and wash conditions. Oligonucleotides can be synthesized on an Applied BioSystems oligonueleotide synthesizer according to specifications provided by the manufacturer.

One method for amplification of target nucleic acids, for later analysis by hybridization assays, is known as the polymerase chain ruction ("PCR") or PCR technique. The PCR technique can be applied to detect sequences of the invention in suspected samples using oligonucleotide primers spaced apart from each other and based on the genetic sequence set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Salki et al., Nature (1986) 324:163–166; and Scharf et al., Science (1986) 233:1076–1078. Also see U.S. Pat. Nos. 4,683,194; 4,683,195; and 4,683,202, the text of each patent is herein incorporated by reference. Additional methods for PCR amplification are described in: PCR Technology: Principles and Applications for DNA Amplification ed. HA Erlich, Freeman Press, New York, N.Y. (1992); PCR Protocols: A Guide to Methods and Applications, eds. Innis, Gelfiand, Snisky, and White, Academic Press, San Diego, Calif. (1990); Mattila et al. (1991) Nucleic Acids Res. 19: 4967; Eckert, K. A. and Kunkel, T. A. (1991) PCR Methods and Applications 1: 17, and; PCR, eds. McPherson, Quirkes, and Taylor, IRL Press, Oxford, which are incorporated herein by reference.

Vectors suitable for replication in mammalian cells are known in the art, and can include vital replicons, or sequences that ensure integration of the sequence encoding PAK65 into the host genome. Suitable vectors can include, for example, those derived from simian virus SV40, retroviruses, bovine papilloma virus, vaccinia virus, and adenovirus.

A suitable vector, for example, is one derived from vaccinia viruses. In this case, the heterologous DNA is inserted into the vaccinia genome. Techniques for the insertion of foreign DNA inw the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid shuttle vecWrs that greafly facilitate the construction of recombinant viruses have been described (see, for example, Mackett et al. 1984); Chakrabarti et al. (1985); Moss (1987)). Expression of the heterologous polypeptide then occurs in cells or individuals which are immunized with the live recombinant vaccinia virus.

Such suitable mammalian expression vectors usually contain one or more eukaryotic transcription units that are capable of facilitating expression in mammalian cells. The transcription unit is comprised of at least a promoter element to mediate transcription of foreign DNA sequences. Suitable pwmoters for mammalian cells are known in the art and include vital promoters such as that from simian virus 40 (SV40), cytomegalovirus (CMV), Rons sarcoma virus (RSV), adenovirus (ADV), and bovine papilloma virus (BPV).

The optional presence of an enhancer element (enhancer), combined with the promoter elements described herein, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter (Maniatis et al. (1987) Science 236:1237; Alberts et al. (1989) Molecular Biology of the Cell, 2nd ed.). Enhancer elements derived from viruses can be particularly useful, because they typically have a broader host range. Examples useful in mammalian cells include the SV40 early gene enhancer (Dijkema et al (1985) EMBO J. 4:761) and the enhancer/promoters derived from the long terminal repeat (LTR) of the Rous Sarcoma Virus (Gorman et al. (1982b) Proc. Natl. Acad. Sci. 79:6777) and from human cytomegalovirus (Boshart et al. (1985) Cell 41:521). Additionally, some enhancers are regulatable and become active only in the presence of an inducer, such as a hormone or metal ion (Sassone-Corsi and Boreill (1986) Trends Genet. 2:215; Maniatis et al. (1987) Science 236:1237).

In addition, the transcription unit can also be comprised of a termination sequence and poly(A) addition sequences which are operably linked to the PAK65 coding sequence. The transcription unit can also be comprised of an enhancer sequence which increases the expression of PAK65.

Sequences that cause amplification of the gene may also be desirable, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes PAK65 can be used for transformation of a suitable mammalian host cell. Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216, 4,912,040, 4,740, 461, and 4,959,455 (these patents are incorporated herein by reference). The transformation procedure used depends upon the host to be transformed. Methods for intwduction of heterologous polynucleotides inw mammalian cells are known in the art and include dextran-mediated transfection, calcium phosphate precipitation, polybrene mediated transfection, protoplast fusion, electropotation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocelhlar carcinoma cells (e.g., Hep G2), and a number of other cell lines. As discussed below, cell lines of particular preference are those expressing recombinant hPAK65 constructs having constitutive serine kinase activity, and which more preferably subsequently develop characteristics of a transformed cell.

In the case of expression in insect cells, generally the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. A preferred vector is pAcC13 (Rubinfeld, B. (1991) Cell 65:1033–1042). A preferred expression plasmid is pAcPAK780, which contains a Myc-epitope:hPAK65 fusion construct. A preferred insect cell line is Sf9. The nucleotide sequence of the coding region of the Myc-epitope:hPAK65 joint region of pAcPAK780 is ATG GAG CAG AAG CTG ATC TCC GAG GAG GAC CTG ATG GAG GAA, which continues to the end of the hPAK65 coding sequence in FIG. 2A.

One of the most commonly used transfer vector for introducing foreign genes into AcNPV is pac373. Many other vectors, known to those of skill in the art, have also been designed. These include, for example, pVL985 (which alters the polyhedrin start codon from ATG to ATT, and which introduces a BarnHI cloning site 32 base pairs downstream from the ATT; see Luckow and Summers, Virology (1989) 17:31.

The plasmid usually also contains the polyhedrin polyadenylation signal (Miller et al. (1988) Ann. Rev. Microbiol., 42:177) and a procaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector can also have a second domain called an enhancer, which, if present, is usually distal to the structural gene. Expression can be either regulated or constitutive.

Additionally, the PAK65 polynucleotide or a fragment thereof can be expressed in a bacterial system. Therein, a bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (Raibaud et al. (1984) Armu. Rev. Genet. 18:173]. Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lacWse (lac) (Chang et al. 1977) Nature 198:1056), and maltose. Additional examples include promoter sequences derived from biosynthetic enzymes such as tryptophan (trp) (Goeddel et al. (1980) Nuc. Acids Res. 8:4057; Yelvenon et al. (1981) Nucl. Acids Res. 9:731; U.S. Pat. No. 4,738,921; EPO Pub. Nos. 36,776 and 121,775). The β-lactomase (bla) promoter system (Weissmann (1981). In Interferon 3 (ed. I. Gresser)), bacteriophage lambda PL (Shimatake et al. (1981) Nature 292:128) and T5 (U.S. Pat. No. 4,689,406) promoter systems also provide useful promoter sequences.

In addition, synthetic promoters which do not occur in nature also function as bacterial promoters. For example, transcription activation sequences of one bacterial or bacteriophage promoter can be joined with the opewn sequences of another bacterial or bacteriophage promoter, creating a synthetic hybrid promoter (U.S. Pat. No. 4,551, 433). For example, the tac promoter is a hybrid trp-lac promoter comprised of both trp promoter and lac operon sequences that is regulated by the lac repressor (Areann et al. (1983) Gene 25:167; de Boer et al. (1983) Proc. Natl. Acad. Sci. 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) J. Mol. Biol. 189:113; Tabor et al. (1985) Proc Natl. Acad. Sci. 82:1074). In addition, a hybrid promoter can also be comprised of a bacteriophage promoter and an E. coli operator region (EPO Pub. No. 267,851).

In addition to a functioning promoter sequence, an efficient ribosome binding site is also useful for the expression of the PAK65 gene or fragment thereof in prokaryotes. In E. coli, the ribosome binding site is called the Shine-Dalgarno (SD) sequence and includes an initiation codon (ATG) and a sequence 3–9 nucleotides in length located 3–11 nucleotides upstream of the initiation codon (Shine et al. (1975) Nature 254:34). The SD sequence is thought to promote binding of mRNA to the ribosome by the pairing of bases between the SD sequence and the 3' and of E. coli 16S rRNA (Steitz et al. (1979). In Biological Regulation and Development: Gene Expression (ed. R. F. Goldberger)). To express eukaryotic genes and prokaryotic genes with weak ribosome-binding site (Sambrook et al. (1989) "Expression of cloned genes in Escherichia coli." In Molecular Cloning: A Laboratory Manual).

PAK65 can be expressed intracellularly. A promoter sequence can be directly linked with the PAK65 gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase (EPO Pub. No. 219,237).

Fusion proteins provide an alternative to direct expression. Typically, a DNA sequence encoding the N-terminal portion of an endogenous bacterial protein, or other stable protein, is fused to the 5' end of heterologous PAK65 coding sequences. Upon expression, this construct will provide a fusion of the two amino acid sequences. For example, the bacteriophage lambda cell gene can be linked at the 5' terminus of the PAK65 gene or fragment thereof and expressed in bacteria. The resulting fusion protein preferably retains a site for a processing enzyme (factor Xa) to cleave the bacteriophage protein from the PAK65 gene or fragment thereof (Nagai et al. (1984) Nature 309:810). Fusion proteins can also be made with sequences from the lacZ (Jia et al. (1987) Gene 60:197), trpE (Allen et al. (1987) J. Biotechnol. 5:93; Makoff et al. (1989) J. Gen. Microbiol. 135:11), and Chey (EPO Pub. No. 324,647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the PAK65 polypeptide. Through this method, mature PAK65 polypeptides can be isolated (Miller et al. (1989) BioFFechnology 7:698). A preferred recombinantly derived fusion contains an Myc-epitope (with an added methionine: MEQKLISEEDL) fused to the N-terminal of a PAK polypeptide or fragment. An antibody specific for this Myc epitope allows isolation and or identification (as in an assay) of the fusion protein. One such embodiment is the construct found inhPAK65 expression vector pAcPAK780. Another preferred system is a fusion with glutathione-S-transferase ("GST"; available from Pharmacia) at the C-terminal end of hPAK65 or its fragment. The recombinant fusion protein is readily isolated by its ability to bind to glutathione attached to solid support followed by elution of the fusion with glutathione. A most preferred embodiment of this type is found in plasmid pGSTPAKette which encodes the recomcontains GST fused in referred to as GST-PAKette, which contains GST fused to a hPAK65 protein fragment amine acids 49 to 113 and which retains the ability to specifically bind rac1 or CDC42 Hs. This domain of hPAK65 contains the rac1 binding domain. The amine acid sequence of GST-PAKette is provided in FIG. 10.

Alternatively, hPAK65 polypeptides can also be secreted from the cell by creating chimetic DNA molecules that encode a fusion protein comprised of a signal peptide sequence fragment that provides for secretion of the hPAK65 polypeptides in bacteria (U.S. Pat. No. 4,336,336). The signal sequence fragment typically encodes a signal peptide comprised of hydrophobic antino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vive or in vitro encoded between the signal peptide fragment and the hPAK65 polypeptide.

DNA encoding suitable signal sequences can be derived from genes for secreted bacterial proteins, such as the E. coli outer membrane protein gene (ompA) (Masui et al. (1983), in: Experimental Manipulation of Gene Expression; Ghrayeb et al. (1984) EMBO J. 3:2437) and the E. coli alkaline phosphatase signal sequence (phoA) (Oka et al. (1985) Proc. Natl. Acad. Sci. 82:7212). As an additional example, the signal sequence of the alpha-amylase gene from various Bacillus swains can be used to secrete heterologous proteins from B. subtilis (Palva et al. (1982) Proc. Natl. Acad. Sci. USA 79:5582; EPO Pub. No. 244,042).

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids)capable of stable maintenance in a host, such as bacteria. The replicon will have a replication system, thus allowing it to be maintained in a procaryotic host either for expression or for cloning and amplification. In addition, a replicen can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector can be selected, depending upon the effect of the vector and thehPAK65 polypeptide on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EPO Pub. No. 127, 328). Integrating vectors can also be comprised of bacteriophage or transposon sequences.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (Davies et al. (1978) Annu. Rev. Microbiol. 32:469). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* (Palva et al. (1982) Proc. Natl. Acad. Sci. USA 79:5582; EPO Pub. Nos. 36,259 and 63,953; PCT WO 84/04541), *Escherichia coli* (Shimatake et al. (1981) Nature 292: 128; Ammann et al. (1985) Gene 40:183; Studier et al. (1986) J. Mol. Biol. 189:113; EPO Pub. Nos. 36,776, 136,829 and 136,907; UK Patent Application Serial No. 8418273), *Streptococcus cremoris* (Powell et al. (1988) Appl. Environ. Microbiol. 54:655) *Streptococcus lividans* (Powell et al. (1988) Appl. Environ. Microbiol. 54:655), *Streptomyces lividans* (U.S. Pat. No. 4,745,056).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electropotation. Transformation procedures usually vary with the bacterial species to be transformed. See e.g., (Masson et al. (1989) FEMS Microbiol. Lett. 60:273; Palva et al. (1982) Proc. Natl. Acad. Sci. USA 79:5582; EPO Pub. Nos. 36,259 and 63,953; P.C.T. WO 84/04541, Bacillus), (Miller et al. (1988) Proc. Natl. Acad. Sci. 85:856; Wang et al. (1990) J. Bacteriol. 172:949, Campylobacter), (Cohen et al. (1973) Proc. Natl. Acad. Sci. 69:2110; Dower et al. (1988) Nucleic Acids Res. 16:6127; Kushner (1978) "An improved method for transformation of *Escherichia coli* with ColE1-derived plasmids. In Genetic Engineering: Proceedings of the International Symposium on Genetic Engineering (eds. H. W. Boyer and S. Nicosia); Mandel et al. (1970) J. Mol. Biol. 53:159; Taketo (1988) Biochim. Biophys. Acta 949:318; Escherichia), (Chassy et al. (1987) FEMS Microbiol. Lett. 44:173 Lactobacillus); (Fiedlet et al. (1988) Anal. Biochem 170:38, Pseudomonas); (Augustin et al. (1990) FEMS Microbiol. Lett. 66:203, Staphylocoecus), (Barany et al. (1980) J. Bacteriol. 144:698; Harlander (1987) "Transformation of *Streptococcus lactis* by electropotation," in: Streptococcal Genetics (ed. J. Ferretti and R. Curtiss III); Perry et al. (1981) Infec. Immun. 32:1295; Powell et al. (1988) Appl. Environ. Microbiol. 54:655; Somkuti et al. (1987) Proc. 4th Evr. Cong. Biotechnology 1:412, Streptococcus).

As discussed herein, minor variations in the amino acid sequence of hPAK65 protein are contemplated as being encompassed by the term hPAK65, providing that the minor variations in the amino acid sequence maintain at least 95%, more preferably at least 99%, and to at least one amino acid difference in homology to the human PAK65 protein encoding sequence presented in FIG. 2A. Such minor variations are likely to occur amongst allelic variants of hPAK65. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatichydroxy family; asparagine and glutamine are an amide-c. ontaining family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or kinase properties of the resulting molecule, especially if the replacement does not involve an amino acid at a p21-binding site or kinase active site. Whether an amino acid change results in a functional peptide can readily be determined by assaying the specific activity of the polypeptide derivative. Assays are described in detail herein.

Fragments or analogs of hPAK65 can be prepared by those of ordinary skill in the art. Preferred amino- and carboxy-termini of fragments or analogs occur near boundaries of functional domains. For example, such functional domains include domains conferring the property of binding to form an hPAK65-p21 protein complex, protein kinase domain, autophosphorylation domain, and domains conferring the property of modulating hPAK65-related signal transduction pathways of cells. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function, such as the kinase domain as provided in the Example section. Methods to identify protein sequences that fold into a known three-dimensional structure are known (Bowie et al. (1991) Science 253: 164). Thus, the foregoing examples demonstrate that those of skill in the art can recognize sequence motifs and structural conformations that may be used to define structural and functional domains in an hPAK65 sequence.

Fragments or analogs comprising substantially one or more functional domalps may be fused to heterologous polypeptide sequences, wherein the resultant fusion protein exhibits the functional properties conferred by the hPAK65 fragment. For example, fusion protein GST-PAKette (containing amine acids 49 to 113) retains the ability to specifically bind rac1 and CDC42Hs. Alternatively, polypeptides wherein one or more functional domain have been deleted will exhibit a loss of the property normally conferred by the missing fragment. For example, an hPAK65 N-terminal truncation protein containing nucleotides 1065–2248 did not retain serine kinase activity.

Although one class of preferred embodiments are fragments having amino- and/or carboxy-termini corresponding to amine acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunelogical reactivity, amino- or carboxyl-terminal residue modification, or other copsideratiops.

In addition to fragments, analogs of hPAK65 can be made. Such analogs may include one or more deletions or additions of amine acid sequence, either at the amino- or carboxy-termini, or internally, or both; analogs may further include sequence transpositions. Analogs may also comprise amine acid substitutions, preferably conservative substitutions. Additionally, analogs may include heterologous sequences generally linked at the amino- or carboxy-terminus, wherein the heterologous sequence(s) confer a functional property to the resultant analog which is not inherent to a native hPAK65 protein. However, analogs must comprise a segment of 25 amino acids that has substantial identity to a portion of the native protein amino acid sequence. Preferred amino acid substitutions are those which: (1) reduce susceptibility to proteolysis, (2) reduce susceptibility to oxidation, (3) alter binding affinity for forming hPAK65-p21 protein complexes, (4) alter binding affinity for forming hPAK65 complexes to proteins subtrates for serine kinase activity, and (4) confer or modify other physicochemical or functional properties of such analogs. Analogs can include various muteins of a hPAK65 sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts.

A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles, (1984) Creighton (ed.), W. H. Freeman and Company, New York; Introduction to Protein Structure, (1991), C. Branden and J. Tooze, Garland Publishing, New York, N.Y.; and Thornton et al. (1991) Nature 354: 105; which are incorporated herein by reference).

It can be advantageous to employ a peptide analog of hPAK65, or a portion thereof, as a pharmaceutical agent or as a commercial research reagent. For example, a peptide analog of hPAK65 having high affinity for binding a p21 protein can be used as a competitive inhibitor of hPAK65-p21 protein complex formation by competing with native hPAK65 for binding to a p21 protein.

In addition to polypeptides consisting only of naturally-occuring amino acids, peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15: 29; Veber and Freidinger (1985) TINS p.392; and Evans et al. (1987) J. Med. Chem 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human PAK65, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications"(general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R. G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:440–404 (—C(OH)CH$_2$—); and Hruby, V. J., Life Sci (1982) 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological proponies (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s)

on the peptidomimetic that are predicted by quantitative structure-activity data and/or molecular modeling. Such non-interfering positions generally are positions that do not form direct contacts with the macromolecules(s) (e.g., are not contact points in hPAK65-p21 complexes) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

Human PAK65 cDNA sequences are identified and genomic clones can be isolated by screening a human genomic clone library, such as a human genomic library in yeast artificial chromosomes, cosraids, or bacteriophage λ (e.g., λ Charon 35), with a polynucleotide probe comprising a sequence of about at least 30 contiguous nucleotides (or their complement) of the cDNA sequence shown in FIG. 2A. Typically, hybridization and washing conditions are performed at high stringency according to conventional hybridization procedures. Positive clones are isolated and sequenced. For illustration and not for limitation, a full-length polynucleotide corresponding to the sequence of FIG. 2A may be labeled and used as a hybridization probe to isolate genomic clones from a human genomic clone library in λEMBL4 or λGEM11 (Promega Corporation, Madison, Wis.); typical hybridization conditions for screening plaque lifts (Benton and Davis (1978) Science 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1 \times 10^5$ to $1 \times 10^7$ cpm/ml of denatured probe with a specific activity of about $1 \times 10^8$ cpm/μg, and incubation at 42° C. for about 6–36 hours. Prehybridization conditions are essentially identical except that probe is not included and incubation time is typically reduced. Washing conditions are typically 1–3× SSC, 0.1–1% SDS, 50°–70° C. with change of wash solution at about 5–30 minutes. Cognate human sequnces, including allelic sequences, can be obtained in this manner.

Nonhuman cDNAs and genomic clones (i.e., cognate nonhuman PAK65 genes) can be analogously isolated from various nonhuman cDNA and genomic clone libraries available in the art (e.g., Clontech, Palo Alto, Calif.) by using probes based on the sequences shown in FIG. 2A, with hybridization and washing conditions typically being less stringent than for isolation of human clones. A most preferred embodiment is a PAK65 gene from mouse.

Polynuclcotides comprising sequences of approximately 30–50 nucleotides, preferably at least 100 nucleotides, corresponding to or complementary to the nucleotide sequence shown in FIG. 2A can serve as PCR primers (at least 10 nucleotides) and/or hybridization probes for identifying and isolating germline genes closely related to hPAK65. These germline genes may be human or may be from another mammalian species, preferably primates or mice. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 2A. Human genomic libraries are publicly available or may be constructed de novo from human DNA.

Genomic clones of PAK65, particularly the murine cognate PAK65 gene, may be used to construct homologous targeting constructs for generating colis and transgenic nonhuman animals having at least one functionally disrupted PAK65 allele, preferably homozygous for ablated PAK65 alleles. Guidance for construction of homologous targeting constructs may be found in the art, including: Rahemtulla et al. (1991) Nature 353: 180; Jasin et al. (1990) Genes Devel. 4: 157; Koh et al. (1992) Science 256: 1210; Molina et al. (1992) Nature 357: 161; Grusby et al. (1991) Science 253: 1417; Bradley et al. (1992) BioTechnology 10: 534, incorporated herein by reference). Homologous targeting can be used to generate so-called "knockout" mice, which are heterozygous or homozygous for an inactivated PAK65 allele. Such mice may be sold commercially as research animals for investigation of PAK65-dependent conditions, such as cell structural integrity, neoplasia, cell proliferation, signal transduction, drug screening, and other uses.

Chimeric targeted mice are derived according to Hogan, et al., Manipulating the Mouse Embryo: A Laboratory Manual, Cold Spring Harbor Laboratory (1988) and Teratocarcinomas and Embryonic Stem Cells: A Practical Approach, E. J. Robertson, ed., IRL Press, Washington, D.C., (1987) which are incorporated herein by reference. Embryonic stem cells are manipulated according to published procedures (Teratocarcinomas and Embryonic Stem Cells: A Practical Approach, E. J. Robertson, ed., IRL Press, Washington, D.C. (1987); Zjilstra et al. (1989) Nature 342:435; and Schwartzberg et al. (1989) Science 246: 799, each of which is incorporated herein by reference).

Additionally, a PAK65 cDNA or genomic gene copy may be used to construct transgenes for expressing PAK65 polypeptides at high levels and/or under the transcriptional control of transcription control sequences which do not naturally occur adjacent to the PAK65 gene, as discussed above. For example but not limitation, a constitutive promoter (e.g., a HSV-tk or pgk promoter) or a cell-lineage specific transcriptional regulatory sequence (e.g., an albumin, elastase, or CD4 or CD8 gene promoter/enhancer) may be operably linked to a PAK65-encoding polynucleotide sequence to form a transgene (typically in combination with a selectable marker such as aneo gene expression cassette). Such transgenes can be introduced into cells (e.g., ES cells, hematopoietic stem cells, cultured primary hepatocytes) and transgenie cells and transgenie nonhuman animals may be obtained according to conventional methods. Transgenie cells and/or transgenie nonhuman animals may be used to screen for antineoplastic agents and/or to screen for potential cell proliferation modulating agents, as overexpression of PAK65 or inappropriate expression of PAK65 may result in a hyperproliferative state or hypoproliferative state.

The antisense oligonucleotides of the invention can be synthesized by any of the known chemical oligonucleotide synthesis methods. Such methods are generally described, for example, in Winnacker, From Genes to Clones: Introduction to Gene Technology. VCH Verlagsgesellschaft mbH (H., Ibelgaufts trans. 1987). Any of the known methods of oligonucleotide synthesis can be utilized in preparing the instant antisense oligonucleotides. The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry. Antisense oligonucleotides hybridizable with any portion of the mRNA transcript can be prepared by the oligonucleotide synthesis methods known to those skilled in the art. While any length oligonucleotide can be utilized in the practice of the invention, sequences shorter than 12 bases may be less specific in hybridizing to the target PAK65 mRNA, and may be more easily destroyed by enzymatic digestion. Hence, oligonucleotides having 12 or more nucleotides are preferred. Sequences longer than 18 to 21 nucleotides may be somewhat less effective in inhibiting PAK65 translation because of decreased uptake by the target cell. Thus, oligomers of 12–21 nucleotides are most preferred in the practice of the present invention, particularly oligomers of 12–18 nucleotides. Oligonucleotides complementary to and hybridizable with any portion of the PAK65 mRNA transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5'-terminal region of the PAK65 mRNA transcript are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome is postulated to unravel the antisense/sense duplex to permit translation of the message. (see, e.g. Shakin, J. Biochemistry 261, 16018 (1986)). The antisense oligonucleotide is preferably directed to a site at or near the ATG initiation codon for protein synthesis. Oligonucleotides complementary to a portion of the PAK65 mRNA including the initiation codon are preferred. While antisense oligomers complementary to the 5'-terminal region of the PAK65 transcript are preferred, particularly the region including the initiation codon, it should be appreciated that useful antisense oligomers are not limited to those complementary to the sequences found in the translated portion of the mRNA transcript, but also includes oligomers complementary to nucleotide sequences contained in, or extending into, the 5'- and 3'-untranslated regions. Antisense nucleotides or antisense expression constructs can find use to screen for antineoplastic agents and/or to screen for potential cell proliferation modulating agents, as inappropriate expression of PAK65 may result in a hyperproliferative state or hypoproliferative state.

As been determined herein, there exists a human protein, referred to as hPAK65, which is a 65 kDa protein (as determined by SDS-PAGE under reducing conditions; molecular weight based on deduced amino acid sequece is 56.5 kDa) which interacts in a GTP dependent manner with rac1 and CDC42Hs but not with rho A. The human PAK65 mRNA is ubiquitously expressed in human tissues. Recombinant hPAK65 exhibits identical specificity as the endogenous p65; both can bind rac1 and CDC42Hs in a GTP dependent manner. The GTP bound forms of rac1 and CDC42Hs induce autophosphorylation of hPAK65 on serine residues only. hPAK65 activated either by rac1 or CDC42HS is phosphorylated on the same sites. Induction of hPAK65 autophosphorylation by rac1 or CDC42Hs stimulates hPAK65 kinase activity towards proteins, e.g. myelin basic protein ("MBP"), and once hPAK65 is activated, rac1 or CDC42Hs are no longer required to keep it active. The affinities of rac1 and CDC42Hs for the non phosphorylated or phosphorylated hPAK65 were similar. Human PAK65 had a marginal effect on the intrinsic GTPase activity of CDC42Hs and a more significant inhibition of the GAP p190 stimulated GTPase activity. These data are consistent with a model in which hPAK65 function as an effector molecule for rac1 and CDC42Hs.

Accordingly, the hPAK65 nucleic acids and polypeptides of the invention find particular use by providing a new protein kinase activity, in effecting or modulating human rac1 and CDC42Hs related pathways, in identifying hPAK65-related pathways and disease conditions, and in identifying agents that effect or modulate hPAK65-activity and related pathways. Such p21 protein modulating agents can provide novel chemotherapeutic agents for treatment of neoplasia, lymphoproliferative conditions, arthritis, angiogenesis, inflammation, autoimmune diseases, apoptosis, and the like.

The present inventors have determined that certain p21 proteins bind to hPAK65 to form a high affinity intermolecular complex under physiological conditions, and that these complexes are detected by numerous assays including a modified "overlay assay" and ELISA. p21 protein-hPAK65 complexes are targets for agents capable of modulating certain p21 protein dependent (preferably rac1 and CDC42Hs) andhPAK65-dependent pathways, and particularly are target for novel chemotherapeutic or chemopreventative antineoplastic and immunomodulatory agents. For example, agents which alter rac1:hPAK65 interactions in neoplastic and/or preneoplastic cells may be developed as potential human therapeutic drugs. Candidate antineoplastic agents may be identified by their ability to inhibit rac1:hPAK65 complex formation in vitro and/or in vivo and/or inhibit hPAK65 protein kinase function in vitro and/or in vivo (e.g., block the ability of hPAK65 to phosphorylate cellular targets downstream in a hPAK65-dependent pathway). Accordingly, methods of identifying antineoplastic and immunomodulatory agents are now provided by the invention.

Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemicallyinduced carcinogenesis, and (6) ability to induce a more differentiated phenotype in transformed cells to which the agent is applied.

Since hPAK65 is abundant in neutrophils, agents which enhance or inhibit hPAK65 activity may serve as immunomodulatory agents, for example, to attenuate an inflammatory reaction, graff-venus-host reaction, or autoimmune condition, neurodegenerative diseases, neoplasia, and the like.

One category of assay in which hPAK65-modulating agents (e.g., candidate antineoplastic agents) may be identified is a binding inhibition assay, wherein agents are individually (or in pools) evaluated for their ability to inhibit formation of a binding complex comprising a p21 protein polypeptide) preferably rac1 or CDC42Hs) bound to a hPAK65 polypeptide under aqueous binding conditions in which p21-protein:hPAK65 binding occurs in the absence of the agent (see Examples). hPAK65 modulating agents (e.g., candidate antineoplastic agents) can be identified by screening for agents which interfere with the formation of or activity of functional p21-protein:hPAK65 complexes. Agents which inhibit binding of rac1 polypeptides to hPAK65 polypeptides are identified as hPAK65-modulating agents (e.g., candidate antineoplastic agents).

The screening assays of the present invention may utilize isolated or purified forms of the assay components (hPAK65 polypeptides and p21 protein polypeptides, preferably rac1 and CDC42Hs). This refers to polypeptides of the present invention which have been separated from their native environment (e.g., a cytoplasmic or nuclear fraction of a cell) or by recombinant production, to at least about 10-50% purity. A substantially pure composition includes such polypeptide(s) or complexes that are approaching homogeneity, i.e., about 80-90% pure, preferably 95-99% pure, and most preferably greater than 99% pure. Preferred embodiments include binding assays which use rac1 or CDC42Hs in combination with hPAK65 polypeptides which are produced by recombinant methods or chemically synthesized.

Additional preferred embodiments comprise p21 protein or hPAK65 analogs that have superior stabilities as experimental reagents. For example, preferred analogs may be resistant to degradation by proteolytic activities present in the binding reaction(s), and/or may be resistant to oxidative inactivation. Such analogs may include amino acid substitutions which remove proteolytic cleavage sites and/or replace residues responsible for oxidative inactivation (e.g., methionine, cysteine). However, the analogs must be functional in at least the control binding assay(s); therefore, analogs comprising amino acid substitutions which destroy or significantly degrade the functional utility of the analog in the binding assay are not employed for such assays. A preferred hPAK65 p21 protein binding polypeptide contains hPAK65 amino acids 49 to 113, with a more preferred form as fusion protein GST-PAKette. A preferred polypeptide for kinase inhibition assays is a constitutively active hPAK65. Preferred polypeptides of this are truncations missing the regulatory domain that inhibits kinase activity or are glutrunic or aspartic acid substitutions for serine 380, serine 383 and/or threonine 384. Preferred p21 protein analogs have an identifying tag moiety attached, preferably a peptide epitope tag recognizable by an antibody. Preferred tags are the Myc-epitope and Glu-Glu peptide tags as provided in the Examples. Also preferred are hPAK65 having C-terminal mutations where the amino acids 489–491 (i.e., Ser-Ser-Leu) are replaced non-conservatively or are removed. One constitutively active hPAK65 embodiment of this type has a deletion of amino acids 482 to 506. A preferred embodiment has both the previously discussed myc-epitope tagged rhPAK65 and the 482–506 deletion.

These methods of screening may involve labelling a p21 protein or hPAK65 polypeptide with any of a myriad of suitable markers, including radiolabels (e.g., $^{125}I$ or $^{32}P$), various fluorescent labels and enzymes, (e.g., glutathione-S-transferase, luciferase, and β-galactosidase). If desired for basic binding assays, the target polypeptide may be immobilized by standard techniques. For example but not for limitation, such immobilization may be effected by linkage to a solid support, such as a chromatographic matrix, microtiter plate well, or by binding to a charged surface, such as a Nylon 66 membrane.

Binding assays generally take one of two forms: immobilized hPAK65 polypeptide(s) can be used to bind labeled p21 protein polypeptide(s), or conversely, immobilized p21 protein polypeptide(s) can be used to bind labeled hPAK65 polypeptides. In each case, the labeled polypeptide is contacted with the immobilized polypeptide under aqueous conditions that permit specific binding of the polypeptides(s) to form a complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the an that additions, deletions, modifications (such as pH) and substitutions (such as KCl substituting for NaCl or buffer substitution) may be made to these basic conditions. Modifications can be made to the basic binding reaction conditions so long as specific binding of p21 protein polypeptide(s) to hPAK65 polypeptides occurs in the control reaction(s). Conditions that do not permit specific binding in control reactions (no agent included) are not suitable for use in inding assays. As determined herein human rho A does not bind to nor activate hPAK65.

Preferably, at least one polypeptide species is labeled with a detectable marker. Suitable labeling includes, but is not limited to, radiolabeling by incorporation of a radiolabeled amino acid (e.g., $^{14}C$-labeled leucine, $^3H$-labeled glycine, $^{35}S$-labeled methionine), radiolabeling by post-translational radioiodination with $^{125}I$ or $^{131}I$ (e.g., Bolton-Hunter reaction and chloramino T), labeling by post-translational phosphorylation with $^{32}P$ (e.g., phosphorylase and inorganic radiolabeled phosphate), fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker. A preferred format is an ELISA asssy, in which a preferred label is a peptide epitope that is specifically recognized by an antibody and that is attached to one of the proteins, for example by chemical or enzymatic conjugation, or preferably by recombinant DNA methods that yield a fusion protein. Radiolabled GTPγS that binds to but is not hydrolyzed by p21 protein GTPases can also be used to label a p21 protein polypeptide in a p21 protein-hPAK65 binding assay.

Additionally, in some embodiments a p21 protein or hPAK65 polypeptide may be used in combination with an accessory protein (e.g., a protein which forms a complex with the polypeptide, preferably in vivo). It is preferred that different labels are used for each polypeptide species, so that binding of individual and/or heterodimeric and/or multimerit complexes can be distinguished. For example, a CDC42Hs polypeptide may be labeled with fluorescein and an accessory polypeptide, e.g p190, may be labeled with a fluorescent marker that fluorescesces with either a different excitation wavelength or emission wavelength, or both. Alternatively, double-label scintillation counting may be used, wherein a polypeptide is labeled with one isotope (e.g., $^3H$) and a second polypeptide species is labeled with a different isotope (e.g., $^{14}C$) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a ruction temperature of about at least 15° C., more preferably 35° to 42° C., and a time of incubation of approximately at least 15 seconds, although longer incubation periods are preferable so that, in some embodiments, a binding equilibrium is attained. Binding kinetics and the thermodynamic stability of bound p21 protein:hPAK65 complexes, preferably rac1:hPAK65 and CDC42Hs:hPAK65 or where hPAK65 is replaced by GST-PAKette, determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (Protein Structures and Molecular Principles, (1984) Creighwn (ed.), W. H. Freeman and Company, New York).

Specific binding of labeled (e.g. peptide tagged) p21 protein or hPAK65 polypeptide to immobilized hPAK65 or p21 protein polypeptide, respectively, is determined by including unlabeled competitor protein(s) (e.g., albumin). After a binding reaction is completed, labeled polypeptide(s) that is/are specifically bound to immobilized polypeptide is detected. For example, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, immunological, autoradiographic or other radiochemical methods, or combinations thereof). In a preferred format, the label is an antibody detectable epitope (tag), wherein the anti-tag antibody can then be detected by methods known in the art, eg. via measuring the enzymatic activity of an alkaline phosphatase conjugated to the antibody.

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a hPAK65 polypeptide and a p21 protein polypeptide in a control binding reaction. Blocking agents are included to inhibit nonspecific binding of labeled protein to immobilized protein and/or to inhibit nonspecific binding of labeled polypeptide to the irammobilization substrate.

In embodiments where a polypeptide is immobilized, covalent or noncovalent linkage to a substrate may be used. Covalent linkage chemistries include, but are not limited to, well-characterized methods known in the an (Kadonaga and Tijan (1986) Proc. Nat. Acad. Sci. (U.S.A.) 83: 5889, which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a p21 protein polypeptide to an hPAK65 polypeptide. Agents that inhibit binding relative to the control reaction(s) are thereby identified as hPAK65-modulating agents and/or candidate antineoplastic agents and/or candidate immunomodulatory agents.

In one variation, GTPase activity and/or GDP- or GTP-binding activity of p21 protein, preferably rac1 or CDC42Hs, is measured as the assay endpoint. The ability of hPAK65 polypeptide to modulate one or more of these guanine nucleotide activities of p21 protein serves as the basis for the screening assay (see Example 1—modified overlay assay; see Example 12). Test compounds which modulate the activity of hPAK65 to modulate a p21 protein guanine nucleotide activities are thereby identified as hPAK65 protein modulators and p21 protein modulators.

Yeast comprising (1) an expression cassette encoding a GAL4 DNA binding domain (or GAL4 activator domain) fused to a binding fragment of hPAK65 capable of binding to a rac1 polypeptide, (2) an expression cassette encoding a GAL4 DNA activator domain (or GAL4 binding domain, respectively) fused to a binding fragment of rac1 (or CDC42Hs) capable of binding to a hPAK65 polypeptide, and (3) a reporter gene (e.g., β-galactosidase) comprising a cis-linked GAL4 transcriptional response element can be used for agent screening in a two-hybrid screening assay. Such yeast are incubated with a test agent and expression of the reporter gene (e.g., β-galactosidase) is determined; the capacity of the agent to inhibit expression of the reporter gene as compared to a contwl culture identifies the agent as a candidate hPAK65-modulating agent or p21 protein-modulating agent.

hPAK65 and rac1 or CDC42Hs polypeptides, especially those portions which form direct contacts in complex, can be used for rational drug design of candidate modulating agents (e.g., antineoplastics and immunomodulators). The substantially purified complexes and the identification of rac1 or CDDC42Hs as a binding partner for hPAK65 as provided herein permits production of substantially pure polypeptide complexes and computational models which can be used for protein X-ray crystallography or other structure analysis methods, such as the DOCK program (Kuntz et al. (1982) J. Mol. Biol. 161: 269; Kuntz I D (1992) Science 257: 1078) and variants thereof. Potential therapeutic drugs may be designed rationally on the basis of structural information thus provided. In one embodiment, such drugs are designed to prevent formation of a protein complex.

Thus, the present invention may be used to design drugs, including drugs with a capacity to inhibit binding of p21 proteins, preferably rac1 or CDC42Hs, to hPAK65. Using the methods as taught herein other p21 proteins are readily tested for there ability to bind to and activate hPAK65.

The design of compounds that interact preferentially with a hPAK65 polypeptide or hPAK65:p21 protein complex can be developed using computer analysis of three-dimensional structures. A set of molecular coordinates can be determined using: (1) crystallographic data, (2) data obtained by other physical methods, (3) data generated by computerized structure prediction programs operating on the deduced amino acid sequence data, or, preferably, a combination of these data. Examples of physical methods that may be used to define structure are, for example, two-dimensional homonuclear correlated spectroscopy (COSY). For those skilled in the an with one-dimensional NMR spectroscopy, COSY provides the kind of information available from a single-frequency decoupling experiment (e.g., which spins are scalar coupled to one another). In a COSY plot, the 1D spectrum lies along the diagonal, and the off-diagonal elements are present at the intersection of chemical shifts of groups that are J coupled. The "fingerprint" region contains ($^1H^N$, $^1H^\alpha$) cross-peaks from the peptide backbone. The degree of resolution of the "fingerprint" region of the COSY map obtained in $H_2O$ is a good predictor of the success of sequence-specific assignments to be obtained without recourse to isotopic labeling. Transferred nuclear Overhauser effect (TRNOE) spectra ($^1H$ NMR) relies on different 2D NOE spectra, and, in essence, looks at the conformation of the ligand just after it has dissociated from the protein. The use of TRNOE presumes, however, that the bound and free ligands are in fast exchange on the chemical shift time scale, which translates to a ligand $K_d$ greater than or equal to about $1 \times 10^{-4}$M. TRNOE methods are useful to cross-check and augment the distance information obtained by other approaches.

It is not intended that the present invention be limited by the particular method used to obtain structural information. Furthermore, it is not intended that the present invention be limited to a search for any one type of drug; one or more of the molecules may be naturally-occurring or may be synthetic, or may be a chemically-modified form of a naturally-occurring molecule.

In some embodiments, it is desirable to compare the structure of hPAK65 protein to the structure of other proteins. This will aid in the identification of and selection of drugs that either selectively affect hPAK65 or have a broad-spectrum effect on more than one species of related polypeptide (e.g., other rac1-related proteins). In one embodiment of the invention an assay for determining hPAK65 protein kinase activity is provided.

In another embodiment of the invention, an hPAK65 kinase inhibition assay is provided, which assay can be used for screening drug libraries or agents for their capability to inhibit an hPAK65 kinase activity. In one embodiment of this invention a method is provided for identifying agents which inhibit hPAK65 kinase activity, said method comprising administering an agent to a reaction mixture containing substantially purified hPAK65, preferably activated hPAK65, a substantially purified substrate, e.g. MBP, and $\gamma$-$^{33}$P-ATP, and then determining the extent to which the agent inhibits phosphorylation of substrate as compared to a control reaction lacking the agent.

Accordingly, also provided is an assay kit for identifying agents which inhibit hPAK65 kinase activity wherein the kits contain substantially purified polypeptide containing hPAK65 or more preferably constitutively activated hPAK65 or a fragment thereof with constitutive activity. Activated hPAK65 can be provided in numerous forms including as the autophosphorylated form, as an analog having at least one autophosphorylation-target serine replaced by an amino acid that mimics phosphoserine, e.g. Glu or Asp (Huang and Erikson (1994) Proc. Natl. Acad. Sci. 91:8960–8963), and as an N-terminal truncated form in which the hPAK65 regulatory domain responsible for inhibiting setinc kinase activity is deleted. The assay kit can further contain a substantially purified substrate, such a MBP, and can further contain a buffered aqueous solution and $\gamma$-$^{33}$P-ATP. Preferred serine-substituted constitutively activated analog forms of hPAK65 are those in which either or both serines at amino acid position 381 or 383 are replaced by glutamic or aspanic acid. The threonine at position 384 may be optionally replaced by glutamic or aspartic acid. Also preferred are hPAK65 having C-terminal mutations where the amino acids 489–491 (i.e., Ser-Ser-Leu) are modified or removed. One embodiment of this type has a deletion of amino acids 482 to 506. A preferred embodiment has both the previously discussed mycepitope tag and the 482–506 deletion.

In one embodiment of the invention a method for inhibiting a hPAK65 kinase is provided which includes the steps of contacting a composition containing a hPAK65 kinase with an agent having the capability to inhibit hPAK65 kinase activity as determined in a hPAK65 kinase inhibition assay described herein. Preferably the composition comprises a body fluid of a mammal, more preferably the body fluid is blood or a blood fraction. Preferably PAK65 is a human PAK65. The method can further include the steps of measuring hPAK65 kinase activity in said body fluid in the presence and absence of said inhibitor and relating said kinase activity to concentration of hPAK65 kinase or substrate for hPAK65 kinase in said composition. The contacting can occur in vivo.

In another embodiment of the invention, a pharmaceutical composition for the control of PAK65 kinase dependent diseases in mammals is provided which includes an agent having the capability to inhibit PAK65 kinase activity as determined in a PAK65 kinase activity assay and a pharmaceutically acceptable carrier.

In yet another embodiment of the invention is provided a method of controlling a PAK65 kinase dependent disease, which includes the steps of administering to a mammal suffering from a PAK65 kinase dependent disease a PAK65 kinase dependent disease controlling amount of an agent having the capability to inhibit PAK65 kinase activity as determined in a PAK65 kinase inhibition activity assay.

A method for identifying compounds which inhibit PAK65 p21-binding activity is also provided. The method includes the steps of administering a compound in admixture with a substantially purified p21 protein to a reaction mixture comprising substantially purified PAK65, and determining the extent to which the agent inhibits binding as compared to a control reaction lacking the compound.

In another embodiment of the invention a method for inhibiting a hPAK65 p21-binding activity is provided, which includes the steps of contacting a composition containing a hPAK65 with an agent having the capability to inhibit hPAK65 p21-binding activity as determined in a hPAK65 p21-binding inhibition assay.

Accordingly, also provided is an assay kit for identifying agents which inhibit or modulate hPAK65 p21-binding activity that includes substantially purified hPAK65. The assay kit can optionally contain a substantially purified p21 protein, preferably rac1 or CDC42Hs, a buffered aqueous solution, GTP$\gamma$S, or an antibody to the Glu-Glu epitope tag attached to the N-terminal of rac1 or CDC42Hs. GTP$\gamma$S is a form of GTP that cannot be hydrolyzed to GDP by p21 GTPases.

A method for identifying agents which inhibit or modulate phosphate release from hPAK65-bound p21 proteins is provided. The method includes the steps of contacting a substantially purified p21 protein with a reaction mixture containing substantially purified hPAK65 to form a p21 protein-PAK65 complex, then contacting the complex with the test agent, and then determining the extent to which the agent inhibits phosphate release as compared to a control reaction lacking the agent. The hPAK65 can be bound to a solid support or can be free in solution.

In another embodiment of the invention a method for inhibiting or modulating phosphate release from hPAK65- bound p21 protein is provided, which includes the steps of contacting a composition containing a hPAK65-bound p21 protein with an agent having the capability to inhibit or modulate phosphate release from hPAK65-bound p21 protein as determined in a phosphate release assay.

Accordingly, also provided is an assay kit for identifying agents which inhibit or modulate such phosphate release. The kit includes substantially purified hPAK65. The assay kit can optionally contain a substantially purified p21 protein, preferably rac1 or CDC42Hs, a buffered aqueous solution, and GTPγP$^{32}$.

The invention now provides for the first time the ability to identify cellular substrates for hPAK65 kinase activity that are involved in hPAK65-related pathways. Appropriate use of the protein and nucleic acid hPAK65 embodiments provided by this invention, preferably with the tissue sources or cell lines indicated herein as expressing hPAK65, and particularly constitutively activated hPAK65, will allow identification of those cellular macromolecules that are phosphorylated when hPAK65 serine kinase activity is activated.

The agents identified by the various embodiments of this invention are all readily adapted to therapeutic use as hPAK65 kinase inhibitors (or as hPAK65-rac1/CDC42Hs binding and/or autophosphorylation inhibitors) for the control of PAK65 kinase dependent diseases in mammals. PAK65 kinase dependent diseases can include hyperproliferative disorders which are initiated/maintained by aberrant PAK65 serine kinase enzyme activity. Examples include cancer, atherosclerosis, and antiangiogenesis (e.g., tumor growth, diabetic retinopathy). It is understood in the art that therapeutically useful kinase inhibiting agents preferably should be selective. PAK65 kinase inhibitors that inhibit many other protein kinases as a result of their lack of specificity are highly cytotoxic. Therefore, routine assays which measure cytotoxicity can be used identify PAK65 inhibitors which are likely to produce undesired side effects due to a lack of selectivity. As a more detailed test of selectivity, compounds should be tested for their ability to inhibit the enzymatic activity of a range of other protein kinases, e.g. classes of protein kinases identified based upon the amino acid(s) that serves as their substrate: kinases that phosphorylate tyrosine, kinases that phosphorylate tyrosine and threonine, and kinases that phosphorylate serine and threonine. Examples of kinases that phosphorylate serine and threonine include RAF, protein kinase A, protein kinase C, and TGF beta receptor. The kinase MEK is an example of kinases that phosphorylate tyrosine and threonine.

In the following discussion of uses of kinase inhibitors, the discussion focuses on hPAK65 protein kinase, however, it should be understood that any discussion here of use of a compound as a hPAK65 kinase inhibitor is generally applicable to use of an agent that is specific for one of the other activities of hPAK65. Whether an agent is specific for hPAK65 kinase activity is readily determined by use of the kinase activity assays set out in the examples.

In order for compounds that inhibit (or modulate) hPAK65 kinase activity or one of its other activities to be therapeutically useful they should be active on intact cells. Several methods are readily available for determining the activity of candidate hPAK65 inhibitors (or modulators) against hPAK65 on intact cells. Phosphorylation of the hPAK65 cellular substrates can be measured using antiphosphoserine antibodies or phosphopeptide fingerprints. Also, additional intracellular signaling events can be measured including calcium flux, inositol phosphate metabolism, cellular proliferation, and cellular DNA synthesis, or any of the other physiological process related to hPAK65 dependent pathways. Preferably, a cell line genetically engineered to express constitutively active hPAK65 may lead to a transformed cell line upon which candidate hPAK65 kinase activity inhibitors can be tested for the ability to decrease hPAK65 kinase activity, decrease overall phosphorylation in a cell, or reverting the cell to a less transformed state.

Candidate agents that inhibit or modulate p21 protein binding to hPAK65 can be further tested against a cell line transformed by a recombinant rac1 that has been altered into a constitutively active form. The rac1-transformed cells have the characteristics of neoplastic cells, e.g. of forming loci and tumors in mice, and can be analyzed for reversion to a more normal state in the presence of candidate agents that inhibit rac 1 activation of hPAK65.

It is likely that solubility of the agents of the present invention both in water and in mildly hydrophobic solvents will enhance the probability that they traverse the cell membrane.

Compounds of this invention may be useful in the form of the free acid, in the form of a salt and as a hydrate. All forms are within the scope of the invention. Basic salts may be formed and are simply a more convenient form for use; in practice, use of the salt form inherently mounts to use of the acid form. The bases which can be used to prepare the salts include preferably those which produce, when combined with the free acid, pharmaceutically acceptable salts, that is, salts whose anions are non-toxic to the animal organism in pharmaceutical doses of the salts, so that the beneficial properties inherent in the free acid are not vitiated by side effects ascribable to the cations. Although pharmaceutically acceptable salts of the acid compound are preferred, all salts are useful as sources of the free acid form even if the particular salt per se is desired only as an intermediate product as, for example, when the salt is formed only for purposes of purification and identification, or when it is used as an intermediate in preparing a pharmaceutically acceptable salt by ion exchange procedures.

Agents within the scope of this invention that have activity as specific inhibitors or modulators of hPAK65 possess therapeutic value as cellular antiproliferative agents for the treatment of certain conditions including, for example, neoplasia, inflammation, lymphoproliferative conditions, arthritis, autoimmune diseases, apoptosis, and the like.

Compounds of the present invention can be administered to a mammalian host in a variety of forms i.e., they may be combined with various pharmaceutically acceptable inert carriers in the form of tablets, capsules, lozenges, troches, hard candies, powders, sprays, elixirs, syrups, injectable or eye drop solutions, and the like depending on the chosen route of administration, e.g., orally or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, derreal, ocular, rectal, nasal inhalation via insufflation and aerosol), and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amount s employed. In addition, the active compound may be incorporated into sustained-release preparations and formulations.

The active compound may also be administered parenterally or intraperitoneally. For purposes of parenteral administration, solutions in sesame or peanut oil or in aqueous proplyene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of suffactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for drop-wise administration to the eye. The therapeutic compounds of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice. The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. Oral administration requires higher dosages. The compounds are administered either orally or parenterally, or topically as eye drops. Dosages can be readily determined by physicians using methods known in the art, using dosages typically determined from animal studies as starting points.

The invention now being generally described, the same will be better understood by reference to the following detailed examples, which are provided for the purpose of illustration only and are not to be considered limiting of the invention unless otherwise specified.

EXAMPLES

Example 1

Identification of Effector Proteins in Neutrophils for rac1 and CDC42Hs.

Figure 1B:
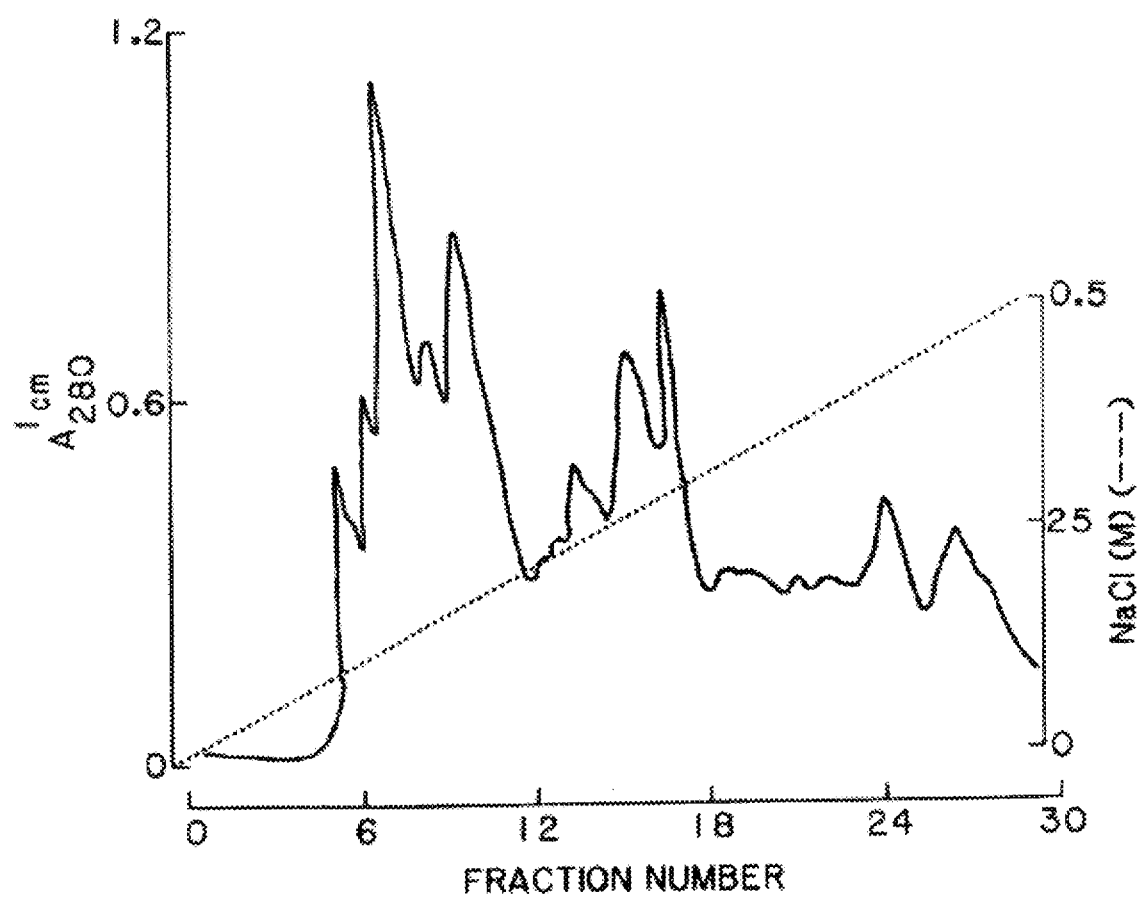

In order to detect whether targets for rac/CDC42Hs exist in humans, an overlay assay was used to detect any such targets in neutrophil cytosol. The overlay assay for GTPase was initially described as a method to detect GTPase activating proteins ("GAP")(Manset et al. 1992, which is incorporated herein by reference) for rho-like proteins; by probing a nitrecellulose filter containing lysate with ($\gamma^{32}$p)GTP bound rho-like proteins it was possible to detect proteins on the filter which can affect the GTP hydrolysis rate, since GAPs catalyze the release of the $\gamma$Pi from GTP, the loss of radiolabeled Pi from the GTPase probe was visualized as clear bands over a dark background. However, by modifying the probing conditions it was discovered by the present inventors that one can detect effector proteins that inhibit the release of Pi as dark bands on the blot. As disclosed herein three major bands clustering near the 68 Kda marker were detected using human neutrophil cytosol. 40 µl of crude or partially purified neutrophil cytosol fraction containing p65 (~80 µg protein) were applied on a 14% SDS PAGE and blotted to a PVDF membrane. The membrane was stained for 30 sec with Coomassie Blue stain to detect transferred proteins, destained for 2 min., and incubated for 30 min with PBS containing 1% BSA, 0.5 mM $MgCl_2$, 0.1% Triton x-100 and 5 mM DTF. 30–50 µl (3–5 µg protein) of either CDC42Hs, human rac1, or human rho A, prepared as recombinant proteins in insect Sf9 cells, were diluted into 200 µl exchange buffer: 25 mM MES, pH 6.5, 50 mM NaCl, 5 mM EDTA, 0.05% Triton x-100 and 1 µl of [$\gamma^{32}$p]GTP (5 µCi, ICN) or [$\beta^{32}$p]GDP (5 µCi, ICN). The proteins were incubated with the exchange buffer for 15 min at room temperature and then were mixed with 10 ml of binding buffer containing 25 mM MES buffer pH 6.5, 0.5 mM GTP, 5 mM $MgCl_2$, 50 mM NaCl, and 5 mM DTT. Immediately, thereafter the nucleotide-loaded protein was used to probe the filter. The mixture was incubated for 5–8 min and washed for five min. with 25 mM MES buffer, pH 6.5, 5 mM $MgCl_2$, 0.05% Triton X-100. The membrane was dried and exposed to a film for 2–3 hours. Three major proteins were detected as targets for rac1/CDC42Hs. It was further determined that these proteins were abundant in cytosolic fractions of neutrophils and HL-60 cells. Accordingly, neutrophils were used as a source for purifying the protein. Fractionation of neutrophil cytosol on a Mono Q column resolved the bands clustering near the 68 kDa marker into three distinct bands of molecular size 62, 65 and 68 kDa, all of which were detected only when the filter was probed with the GTP-bound form of rac1 and CDC42Hs and not with GTP-bound rho A. See FIGS. 1 and 3.

Example 2

Isolation of hPAK65 Protein.

The p65 band, which was the most abundant of the three proteins identified in Example 1, was subsequently isolated and purified. Cytosol was prepared from human neutrophils as previously described (Abo et al. 1994, which is incorporated by reference). All purification steps were performed on columns connected to a FPLC system, at 40° C., flow rate of 1 ml/min, and 1 ml fractions were collected. 10 ml (10mg/ml) of neutrophil cytosol were applied on a Mono Q column (HR5/5 Pharmacia LKB) equilibrated with buffer A: 20 mM Tris-HCl, pH 7.4, 1 mM DTT, 5 mM $MgCl_2$, 1 mM PMSF, 1 µg/ml pepstatin. The proteins were eluted with a 30 ml gradient from 0 to 0.5M NaCl and the collected fractions were assayed for rac1 or CDC42Hs binding by the overlay assay. Fractions containing the p65 protein were pooled and subjected to ammonium sulfate precipitation. Ammonium sulfate grains were added to the mixture over a period of 15 min to achieve 40% saturation. The solution was stirred on ice for an additional 30 min., and subsequently centrifuged at 100,000 g for 15 min in a TLX Beckman ultracentrifuge. The pellet was resuspended in buffer A to its original volume and the fractions were analyzed by the overlay assay. The supernatant obtained by 40% ammonium sulfate sedimentation which contained the desired p65 protein was further purified on a Phenyl Superose column (HR 5/5 Pharmacia LKB) equilibrated with 100 mM Pi buffer, pH 7.2, 1 mM DTT, 5 mM $MgCl_2$, 1 mM PMSF, 1 µg/ml pepstatin and 1.2M ammonium sulfate. The bound proteins were eluted by 30 ml gradient from 1.2M to 0 ammonium sulfate. In the case of the purification of a large amount of starting material (300–500 mg protein), the ammonium sulfate and the Phenyl Superose steps were the first purification procedures followed by the Mono Q fractionation. For this purpose a Hiload Phenyl Sepharose 16/10 column (Pharmacia, LKB) was used. Collected fractions were analyzed by the overlay assay and fractions containing the p65 protein were pooled and desalted into buffer A on a PD 10 column (Pharmacia, LKB). The partially purified p65 was further purified on a Mono S column HR5/5 (Pharmacia LKB) equilibrated with the buffer A. Proteins were eluted by 30 ml gradient 0 to 0.5M NaCl and the fractions were analyzed by the overlay assay. At this stage the p65 polypeptide could be easily identified by Coomassie Blue staining and the band was excised and used for amino acid analysis.

Amino acid sequence was determined as follows. The p65 preparation was purified by SDS-PAGE, following staining with Coomassie Blue G-250, and the protein was excised. After washing, gel pieces were macerated and digested with Achromobacter lyticus endoproteinase Ly-C. Peptides were recovered by sequential washes and separated by tandem hplc using 2.1 mm internal diameter anion exchange and reverse phase columns in series, following previously described procedures (Kawasaki et al. 1990). Fractions were collected and applied directly to an Applied Biosystem 477A pulsed liquid automated sequencer modified for fast cycle chemistry as described (Totty et al. 1992). Digestion of p65 and subsequent amino acid analysis yielded the following amino acid sequence: STMVGTPYWMAPEVVTR, which is closely related to a sequence within the serine/threonine kinase domain of yeast STE20 (Ramer and Davis 1993), and 100% identical to a rat brain serine/threonine kinase, PAK65 (Manset et al. 1994).

Example 3

Isolation of hPAK65 cDNA Clone.

Based on the protein sequence of rat brain PAK65 (Manser et al. 1994) and the amino acid sequence derived from purified p65 determined in Example 2, the oligomers GM749 5' GGGGCCATCCAATAGGGGGTACCNAC-CATNG 3' and GM752 5' ACCGGAGAATTCACCGGCAT-GCCTGAACAGTGG 3' were designed and used to amplify human cDNAs encoding PAK proteins. These oligomers were used to amplify specific PAK cDNAs from several commercially available human cDNA libraries. Although the expected product was detected in several tissue specific libraries, relatively large amounts were detected in a human placenta library. A human placenta library from Stratagene (1994 catalog number 936203) was selected as a source for a cDNA clone. The gel-purified 962 base pair PCR product was amplified in the presence of $^{32}$p dCTP and $^{32}$p dGTP resulting in a radioactive product. This PCR product was used to screen approximately 100,000 recombinant plaques using stringent hybridization conditions (hybridization buffer: 50% formamide, 5X SSC, 5X Denhardt's, 50 mM NaPO$_4$ pH7, and 0.1% SDS at 42° C.; wash: 5xSSC, 0.1% SDS) in order to isolate a full-length cDNA. One positive clone was plaque purified and auto-excised ("in vivo excision") from lambda Zap II according to the manufacturer's protocols to yield the plasmid clone containing the full length human PAK65 cDNA with the sequence presented in FIG. 2A (SEQ ID NO:1), which was designated pBSPAK. The sequence of the cDNA insert contained within the resulting Bluescript plasmid was determined using the dideoxynucleotide chain termination method.

Example 4

Amino Acid Homology.

Figure 2B:
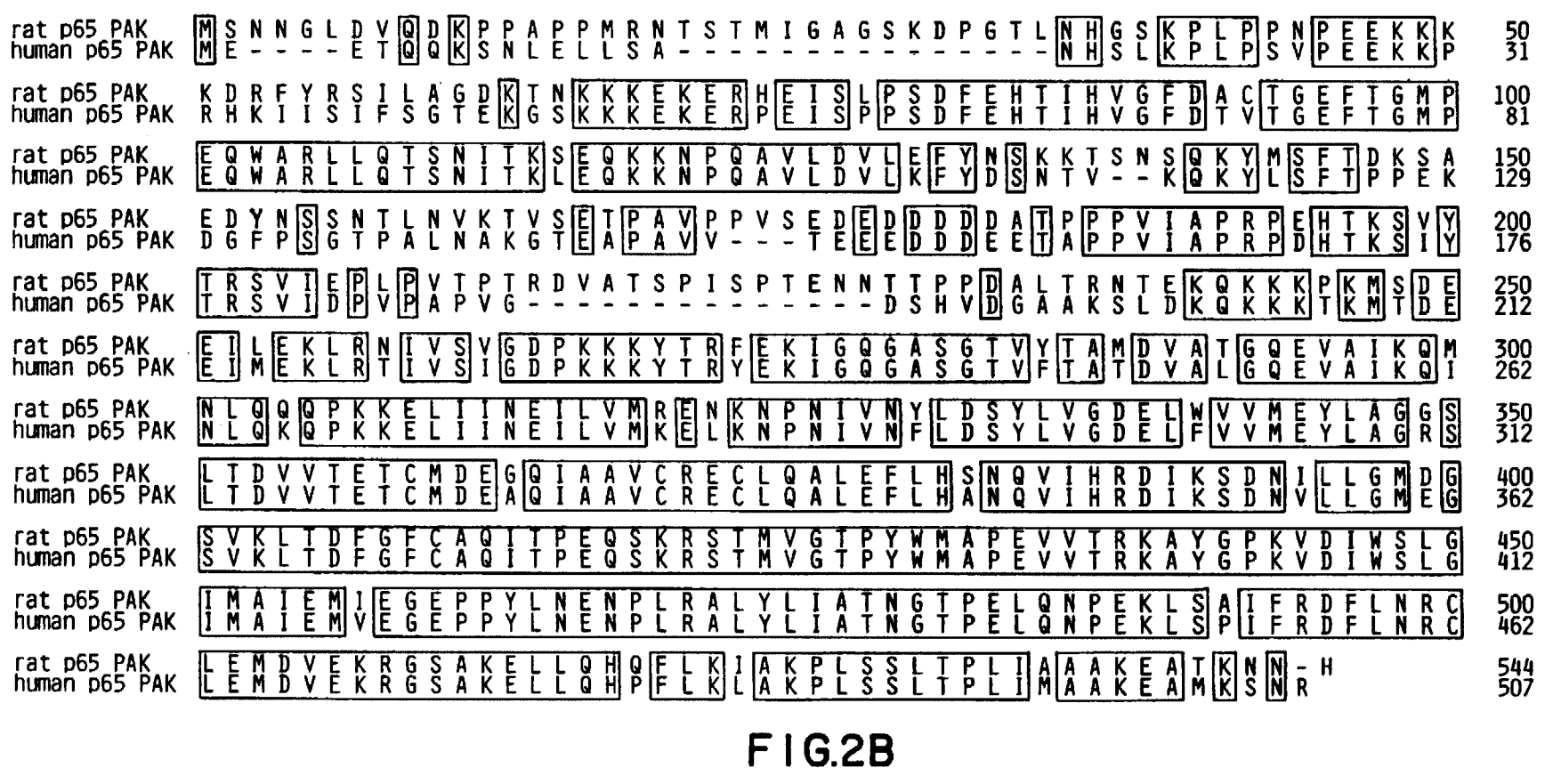
Figure 2C:
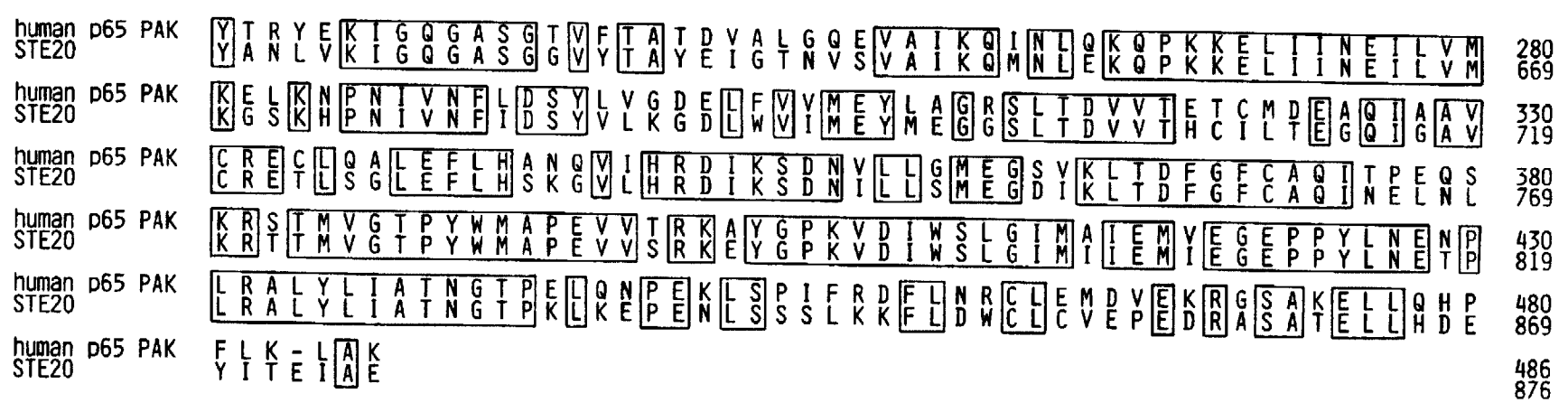

The nucleotide and deduced amino acid sequence of the human PAK65 cDNA, which will be referred to here as hPAK65, is shown in FIG. 2. A full length hPAK65 cDNA clone obtained from a human placental library displayed sequence similarity to the kinase domain of rat brain PAK65 and yeast STE20. Although both rat brain PAK65 and hPAK65 exhibit similar specificity for rac1/CDC42Hs the sequences display only 70% sequence identity at the amino acid level in the rac1/CDC42Hs binding domains. The complete amino acid sequence of hPAK65 shares ~73% identity to the previously isolated PAK65 from rat brain (Manser et al. 1994)(FIG. 2A) and shares more then 95% identity within the kinase domain (amino acids:230–506) (FIG. 2B). In addition, hPAK65 exhibits ~63% identity to the kinase domain of STE20 (position:620–880)(Ramer and Davis 1993)(FIG. 2C). As reported for rat PAK65 (Manser et al. 1994), the rac1 and CDC42Hs binding domain (amino acid 47–113) of hPAK65 also share some similarities to the STE20 regulatory domain. (data not shown).

Example 5

Tissue Distribution of hPAK65.

Figure 3C:
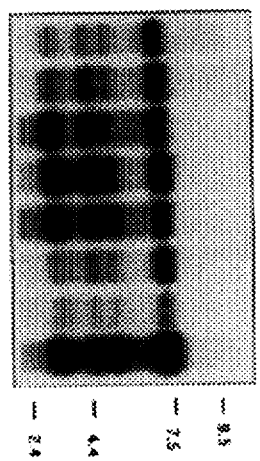
FIGS. 3A, 3B and 3C present Northern blot analysis of hPAK65 in tissue and cell lines. Radioactively labeled probe generated by PCR from the kinase domain (nucleotide sequence 1009–1912) of hPAK65 cDNA was used to hybridize mRNA isolated from various tissues immobilized on northern blots. Autoradiograph was exposed 3 hrs.
Figure 3B:
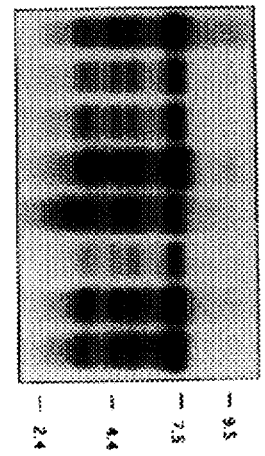
Figure 3A:
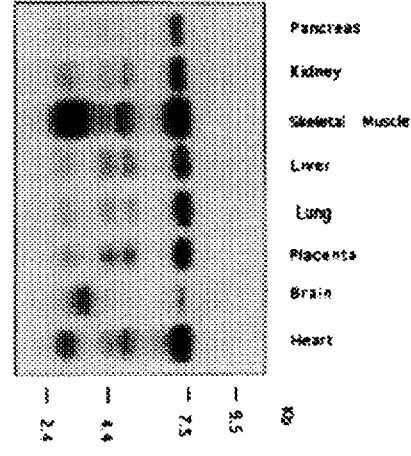

To determine tissue distribution of mRNAs encoding hPAK65 a radioactive PCR product containing the highly conserved kinase domain (base pairs 1009 through 1912) of human PAK cDNA was used to hybridize mRNA derived from 16 human tissues and 8 cancer cell lines immobilized on Northern blots (membrane-bound mRNA is available from Clontech). Since the probe was derived from the kinase domain, the most conserved region amongst hPAK65, rat brain PAK65, and STE20, it was expected that the expression of closely related messages would be analyzed. The hybridization conditions used were as suggested by the manufacturer using ExpressHyb (Clontech) except that the temperature was 72° C. and hybridization time was overnight. The northern blot analysis indicates that hPAK65 related mRNA is ubiquitously distributed among various tissues with higher levels in cells of myeloid origin, namely in skeletal muscle, ovary, thymus, and spleen and 2–3 fold higher in HL-60 cell line (FIG. 3). Four RNA species were detected in most of the tissues with sizes of approximately 7.5 kb, 5 kb, 4.4 kb and 3 kb. The 7.5 kb message was the predominant species in all the tissues except skeletal muscle where the 7.5 kb and the 3 kb mRNA were roughly the same. In contrast, the cell lines HL-60, Molt-4, Raji and SW480 have equal amounts of all four species whereas, in brain a different size mRNA was detected around 3.3 kb. Based on results of genomic Southern blotting under stringent conditions (results not shown; membrane-bound human genomic DNA available from Clontech; conditions were that as suggested by the manufacturer except the hybridization temperature was 64° C. rather than 60° C. and hybridization went overnight), these multiple mRNA are most likely alternatively spliced forms from a single gene (FIG. 3).

In contrast, by the use of the overlay assay, a high level of rat PAK proteins was detected mainly in brain cells (Manset et al. 1994), whereas by nonhem analysis higher expression of hPAK65 in neutrophils and HL-60 cells was found as described herein. It is most likely that the overlay assay ioverlay assay is not sensitive enough to detect PAK in tissues with relatively lower expression of protein, and hence is not a preferred method for determining the tissue distribution of PAK.

Example 6

Production of Recombinant Proteins in Sf9 Cells.

A modifed Glu-Glu epitope tag (Grussenmeyer et al. 1985; modified to Met-Giu-Tyr-Met-Pro-Thr-Asp) was cloned onto the N-terminus of rac 1, CDC42Hs, and rho using a polymerase chain reaction (Grussenmeyer et al. 1985). hPAK65 was myc-epitope tagged (MEQKLISEEDL) by ligating annealed oligomers into the Xba I site (417bp) immediately upstream of the initiation Met of hPAK65. The tagged cDNAs were cloned into the baculovirus expression vector pAcC13. pAcPAK780 contains the myc-tagged hPAK65. 1 g of snap frozen Sf9 pellets, expressing the desired proteins, were Dounce homogenized in 10 ml of Buffer B:50 mM Tris-HCl, pH 7.5, 150 mM NaCl, 5 mM MgCl$_2$, 200 µM GDP, 1 mM Pefabloc, 10 µg/ml leupeptin, 10 µg/ml aprotinin. To remove the particulate fraction, the homogenate was centrifuged at 100,000 g for 15 min. The soluble fraction was applied to 2 ml protein G Sepharose column conjugated either with anti-Glu-Glu or anti-Myc monoclonal antibodies. The column was washed with 10 ml of buffer B lacking GDP, and the protein was eluted with the same buffer containing either the Myc peptide tag or 50 µg/ml of the ED peptide tag (EYMPTD). Fractions were analyzed on a SDS-PAGE, quantitated by the Bradford method, concentrated by a Centricon 10 (Amicon) to 1 mg/ml, aliquoted, snap frozen and stored at –70° C. A fresh aliquot of the protein was used for each assay. Expression of the hPAK65 in Sf9 cells allowed preparation of essentially homogeneous recombinant myc-epitope tagged hPAK65 ("rhPAK65"), which was used for characterization the biochemical properties of hPAK65.

Example 7

The Binding Specificity of hPAK65 to p21 Proteins.

Figure 4:
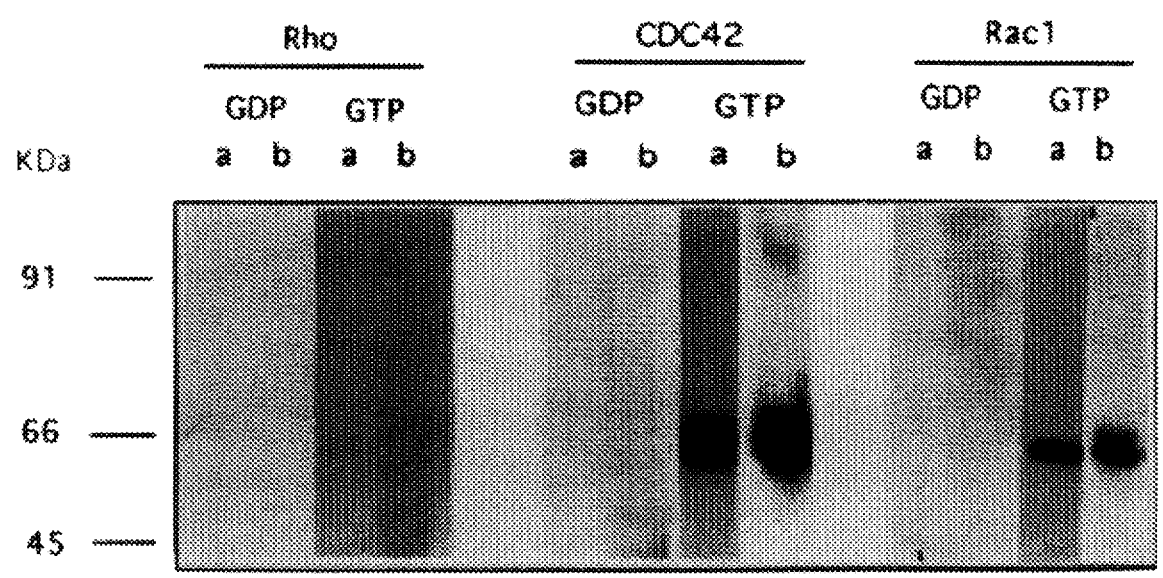
FIG. 4 depicts hPAK65 binding specificity among rho-like proteins. 80 µg of neutrophil cytosol or 2–3 µg of recombinant hPAK65 were applied on SDS-PAGE, blotted onto a PVDF filter, and analyzed by the overlay assay. The filter was probed with the indicated GTPase preloaded with $[\gamma^{32}P]GTP$ or $[\beta^{32}P]GDP$. Lanes a contain recombinant hPAK65 and lanes b contain neutrophil cytosol. Protein molecular weight markers are indicated in kilodaltons.

Recombinant hPAK65 or the endogenous hPAK65 in neutrophil cytosol, was detected only when the filter was probed with [$\gamma^{32}$P]GTP-CDC42Hs and [$\gamma^{32}$P]GTP-rac1 but not with [$\gamma^{32}$P]GTP-rho A (FIG. 4). No proteins were detected when the GTPase was preloaded with [$\beta^{32}$P]GDP, indicating that the hPAK65 protein behaves as an effector molecule for rac1 and CDC42Hs. The relative affinity as judged by the overlay assay is ~3–4 fold higher for CDC42hs than for rac1 (FIG. 4).

Example 8

CDC42Hs and rac1 Induce Autophosphorylation of hPAK65.

Figure 5A:
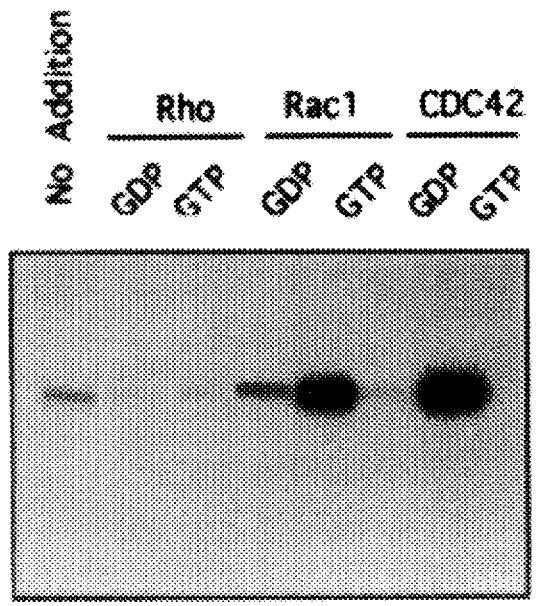
FIGS. 5A, 5B and 5C present results of activation of hPAK65 autophosphorylation.

To determine whether CDC42Hs and rac1 would induce autophnsphorylation of hPAK65, hPAK65 was incubated with the activated form of either rac1 or CDC42Hs in a kinase reaction containing [γ³²P]ATP. Stimulation of autophosphorylation of hPAK65 was observed in both cases (FIG. 5A). No phosphorylation was observed with rho A or by omitting the GTPase and simply adding GTP (FIG. 5A). Phosphorylation occurred in a dose dependent manner only with the GTP or GTPγS form of CDC42Hs or rac1. Maximal phosphorylation was obtained after 15 min at 30° C. (data not shown).

Figure 5B:
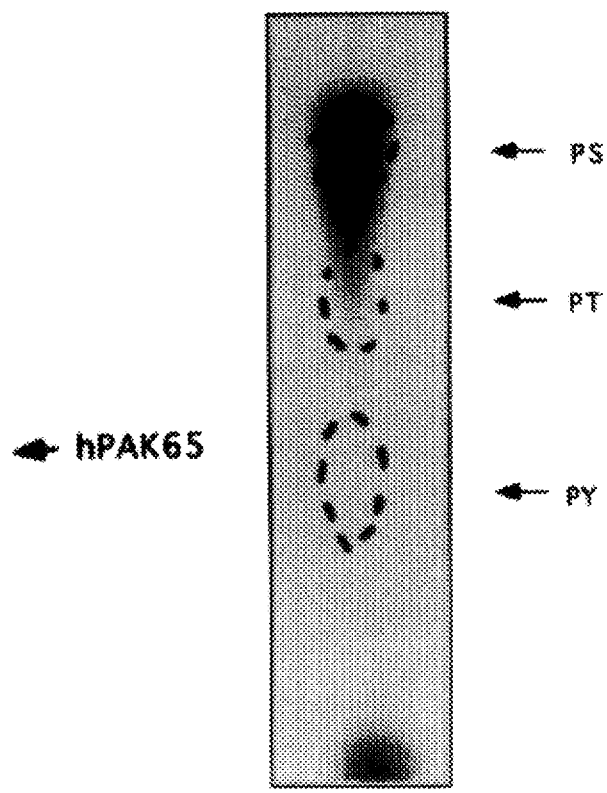

To determine the phosphorylation pattern on hPAK65 induced by rac1 and CDC42Hs, hPAK was subjected to kinase reaction containing either activated rac1 or CDC42Hs. To remove rac1 and CDC42 Hs, the hPAK65 immobilized on beads was washed three times with PBS containing 1% Triton X-100 and the beads were resuspended in 100 mM Tris HCl, pH 6.8, 0.5% SDS, 10 mM DTT, 10% glycerol. The samples were boiled for 3 min and 10 μg of the indicated protease (all from Boehringer) were added. The proteins were digested overnight at room temperature and the samples were analyzed on 16% Tricine gels. The gel was stained with Coomassie Blue, desrained, dried and exposed to film overnight. Phosphoamino acid analysis was performed to determine the location of autophosphorylation. 4 μg (on 50 μl beads) of recombinant hPAK65 were subjected to kinase reaction as described above. The phosphorylated hPAK65 immobilized on Sepharose G beads were washed three time in PBS containing 1% Triton X-100 and then hydrolyzed in 50 μl of 6N HCl at 100° C. for 2 hrs. The beads were removed by centrifugation, and the supernatant was dried and dissolved in 10 μl of pH 3.5 electrophoresis buffer (10:100:1890. pyridine:acetic acid:water). Phosphoamino acids were resolved on a thin layer cellulose plate using the electrophoresis buffer essentially as described before (Cooper et al. 1983). Standards were visualized by staining with 0.2% Ninhydrin in acetone and ³²Pi Labeled residues were detected by autoradiography overnight. Phosphoamino acid analysis indicated that hPAK65 was phosphorylated on setinc residues when activated by CDC42Hs and not on threonine or tyrosine residues (FIG. 5B).

Figure 5C:
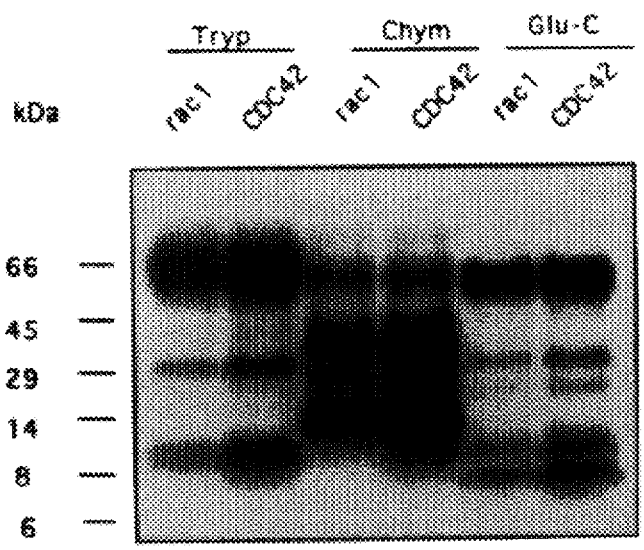

Since rac1 and CDC42Hs share ~72% sequence identity and apparently play different physiological roles, it is conceivable that rac1 and CDC42Hs may activate hPAK65 autophosphorylation on distinct sites. To test this hypothesis hPAK65 was incubated either with rac1 or CDC42Hs in a kinase reaction with [γ³²P]ATP and the phosphorylated protein was digested with three different enzymes: trypsin, chymotrypsin and Glu-C. This treatment resulted in the generation of radiolabeled phosphopeptides which were resolved on 16% a Tricine gel. Identical phosphopeptide profiles were generated from digestion of hPAK65 activated by either rac or CDC42Hs (FIG. 5C). This result suggest that rac and CDC42Hs stimulate hPAK65 to phosphorylate itself on the same serine sites.

Like human neutrophil p65 and rat brain PAK65, recombinant hPAK65 interacted specifically with the activated form of either rac1 or CDC42, and subsequently, if provided with ATP, become autophosphorylated. The data suggest that rac/CDC42Hs mediates hPAK65 autophosphorylation thereby generating an active kinase. The strict requirement for hPAK65 binding and activation by only the GTP-bound form of rac and CDC42Hs indicates that hPAK65 serves as an effector protein for rac/CDC42Hs. In addition, it is most likely, that the relative binding affinity of rac/CDC42Hs for hPAK65 is regulated by their nucleotide state and not by the phosphorylated state of hPAK65. In contrast to the model suggested (Manser et al. 1994), the data disclosed by the present inventors indicates that the phosphorylation state of hPAK65 is not involved in regulating rac/CDC42Hs binding. Phosphorylated and unphosphorylated hPAK65 exhibited comparable affinities for rac1 and CDC42Hs.

Example 9

Phosphorylated hPAK is an Active Kinase.

A kinase assay was performed in order to determine whether hPAK65 had kinase activity towards other proteins and whether that activity was affected by p21 proteins. 1–2 μg of rhPAK65 (bound to protein G Sepharose conjugated with monoclonal Myc antibody) were washed once and incubated in 40 μl of kinase buffer (50 mM Tris —HCl. pH 7.5, 100 mM NaCl, 10 mM MgCl₂, 1 mM MnCl₂) with 1–2 μg of either rac1, rho, or CDC42Hs, which were all previously loaded with GTP or GDP. The reaction was initiated by adding 10 μl of kinase buffer containing 50 μM ATP and 5 μCi [γ³²P]ATP, and incubated for 20 min at 30° C. The reaction was stopped by adding 10 μl of 5X SDS PAGE sample buffer, and boiling for 5 min. Samples were applied to a 14% SDS PAGE, the gel was stained with Coomassie Blue, desrained, dried and exposed to a film for 1–2 hrs. Phosphorylated bands were excised and the incorporated ³²phosphates were counted. In the case of phosphorylation of myelin basic protein ("MBP"), 3 μg of MBP (Sigma) was included in the kinase reaction.

Figure 6A:
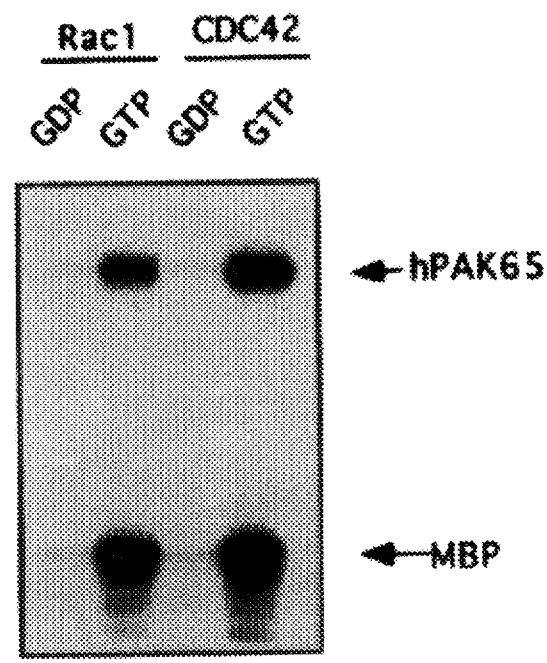
FIGS. 6A, 6B, 6C and 6D depict activation of hPAK65 kinase activity.
Figure 6B:
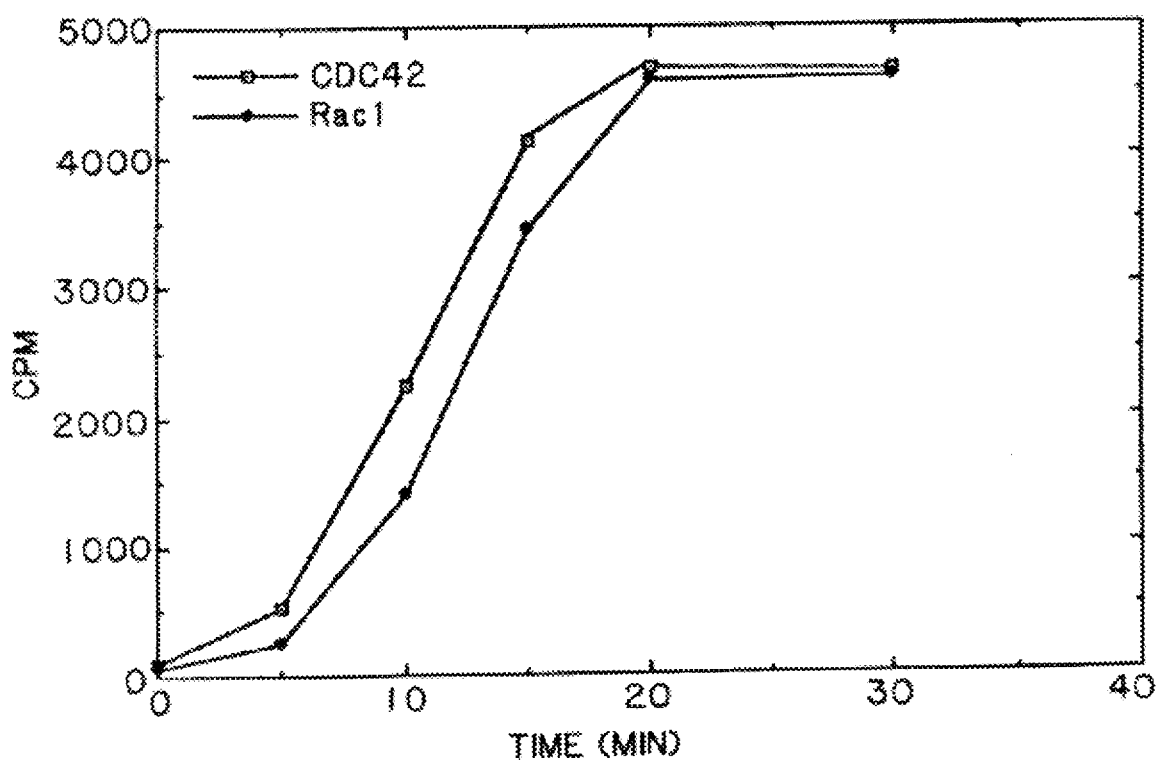

Phosphorylation of hPAK65 induced by rac1 or CDC42Hs stimulates its kinase activity towards MBP substrate (FIG. 6a). Both rac and CDC42Hs were able to stimulate an active hPAK65 kinase in a time dependent manner. Maximal MBP phosphorylation was obtained within 10 min at 30° C. (FIG. 6B).

Example 10

Activated hPAK does not require rac1 or CDC42Hs to Sustain its Kinase Activity.

Figure 6C:
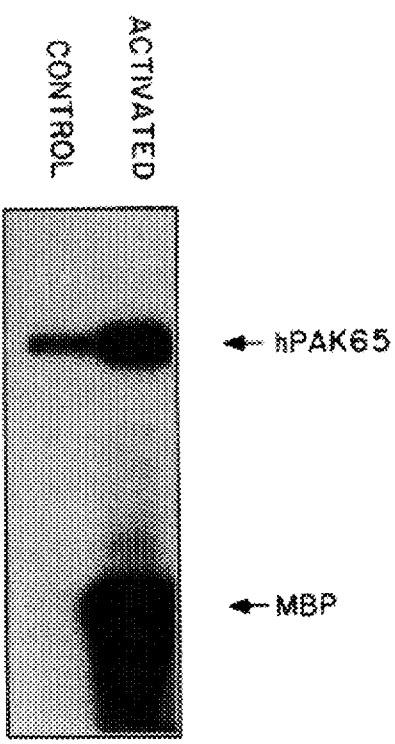
Figure 6D:
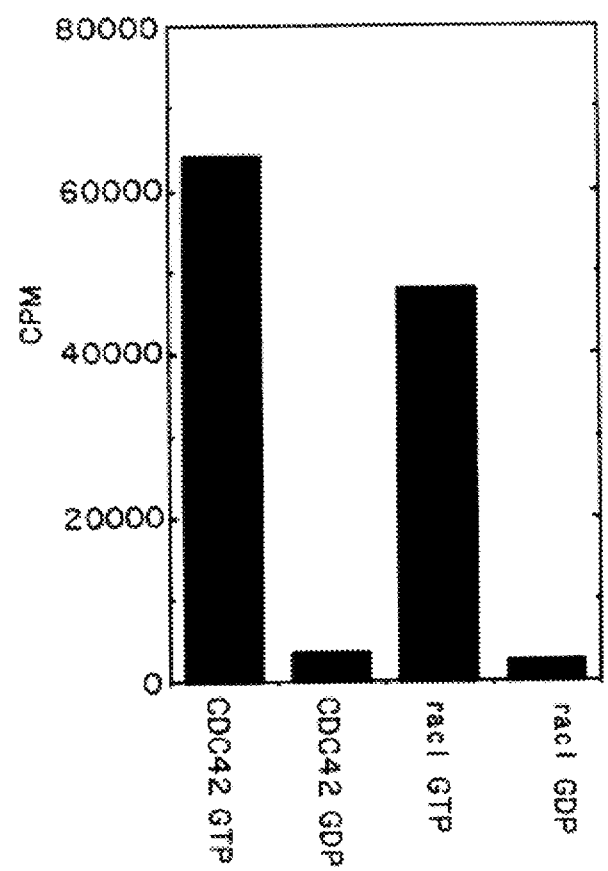

The above experiments clearly demonstrate the requirement for rac 1 CDC42Hs in the activation of hPAK65 antophosphorylation. Whether rac1/CDC42Hs are required for hPAK65 kinase activity was investigated by the following experiment: hPAK65 autophosphorylation was first induced by CDC42Hs in the presence of cold ATP, then hPAK65 and CDC42Hs complex was disrupted by exhaustive washes. The autophosphorylated hPAK65 free of CDC42Hs (confirmed by western blot) was subjected to a second kinase reaction containing [γ³²P]ATP and MBP. Autophosphorylated hPAK65 free of CDC42Hs was sufficient to activate MBP phosphorylation (FIG. 6C). The control hPAK65 was treated exactly the same except that ATP was not included in the first kinase reaction. Lower levels of hPAK65 autophosphorylation were detected on the control hPAK65, which most likely are due to residual levels of unwashed CDC42Hs/PAK complexes. These data suggest that rac and CDC42Hs play an important role in the activation of hPAK65 by stimulating its autophosphorylation but not in the maintenance and regulation of the kinase activity.

Example 11

Comparison of the Binding of CDC42Hs to the Phosphorylated vs. Unphosphorylated hPAK65.

Figure 7:
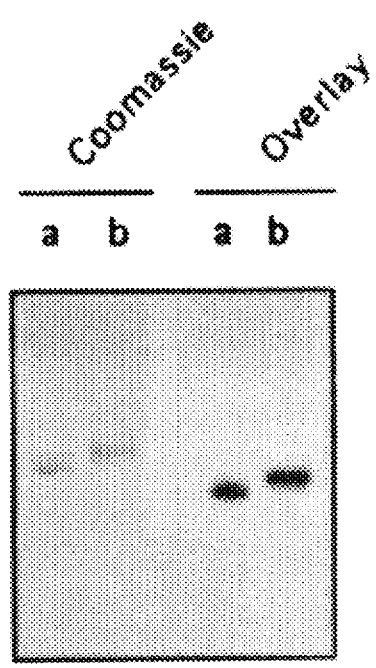
FIG. 7 presents a comparison of the binding of CDC42Hs to phosphorylated and unphosphorylated hPAK65. 2 µg of either unphosphorylated or phosphorylated hPAK65 (induced by CDC42Hs) were run on a SDS PAGE, stained with Coomassie Blue, and were also tested for CDC42Hs binding by the overlay assay. Lane a contains unphosphorylated form and lane b contains the phophorylated form.

Fully phosphorylated and unphosphorylated hPAK65, as judged by mobility shift and kinase reaction, bound equally well to activated CDC42Hs. (FIG. 7) Phosphorylation of hPAK65 most likely serves to activate the kinase of hPAK65 but does not to alter its affinity for rac/CDC42Hs. This result is in contrast to the rat system, wherein it was shown that CDC42 has a reduced affinity for the activated form of rat brain PAK65 and was suggested that phosphorylation of PAK is a mechanism by which rac/CDC42 can be released from PAK once activated (Manser et al. 1994).

Example 12

The Effect of hPAK65 on Intrinsic and Stimulated GTPase Activity.

Figure 8A:
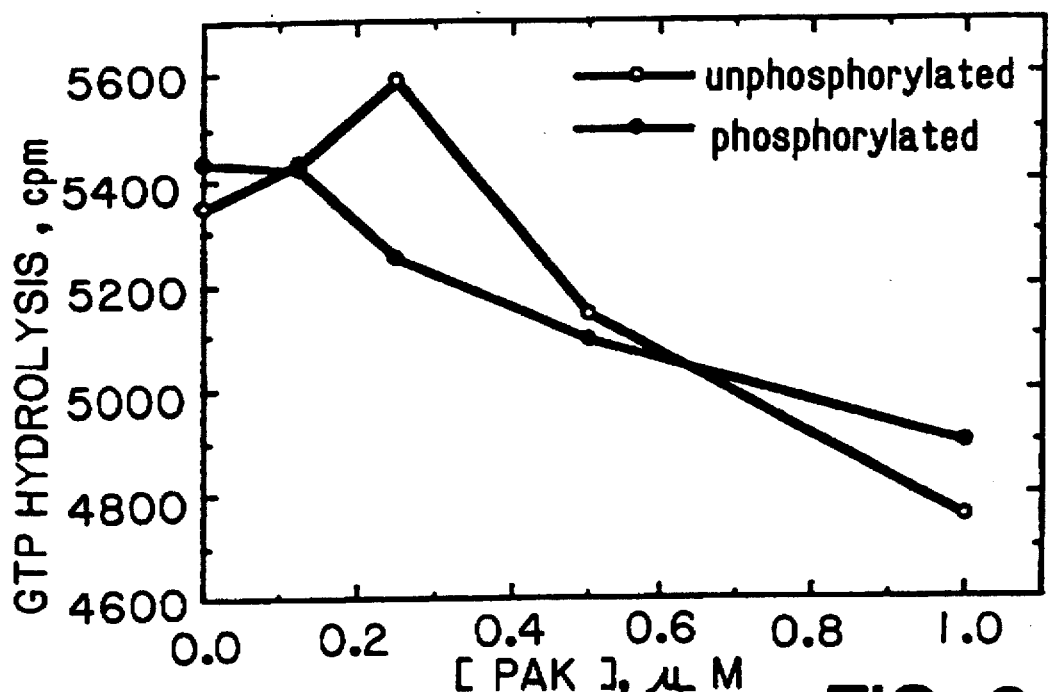
FIGS. 8A and 8B depict the effect of hPAK65 on intrinsic and p190 stimulated GTPase activity of CDC42Hs. 1 nM CDC42Hs preloaded with $[\gamma^{32}P]GTP$ was incubated with the indicated concentrations of unphosphorylated or phosphorylated hPAK65 in the absence (FIG. 8A) or the presence (FIG. 8B) of 20 nM of the catalytic domain of p190, followed by the phosphate released assay.

Since the p65 protein was initially detected by the overlay assay as a potential effector and GTPase inhibitor for rac1/CDC42Hs, the effect of hPAK65 on GTPase activity in solution was examined. Purified CDC42Hs (800 nM) was prebound to 80 nM g-32P-GTP (6000 Ci/mmol) in the presence of 1 mM EDTA for 5 min at 25° C., followed by addition of 19 volumes GAP Assay Buffer (50 mM MES, pH 6, 100 mM NaCl, 5 mM $MgCl_2$) to yield 4 nM γ-32P-GTP-CDC42Hs. 1 nM [γ-$^{32}$P]-GTP-CDC42Hs was incubated with the indicated concentrations of hPAK65, which had been preincubated in the presence or absence of ATP. Reactions were carried out in GAP Assay Buffer containing BSA (0.2 mg/ml BSA, 50 mM MES, pH 6.5, 100 mM NaCl, 5 mM $MgCl_2$) in the presence or absence of 20 nM human p190-catalytic fragment for 5–10 min at 25° C., followed by assay for phosphate release (Shacter 1984). For p 190-stimulated reactions, corresponding reactions in the absence of p190 were performed and the resulting hydrolysis subtracted to yield only p190-dependent activity. p190 is a stimulator of GTPase activity.

hPAK65 does exhibit a marginal effect on CDC42Hs intrinsic GTPase activity (FIG. 8A). Increasing the amount of hPAK65 up to 1000 fold over CDC42Hs inhibited the intrinsic GTPase activity but only by 10–15% (FIG. 8A). Interestingly, activated hPAK65 had an identical effect, suggesting that phosphorylation has no regulatory effect on rac/CDC42Hs intrinsic GTPase activity (FIG. 8A).

Figure 8B:
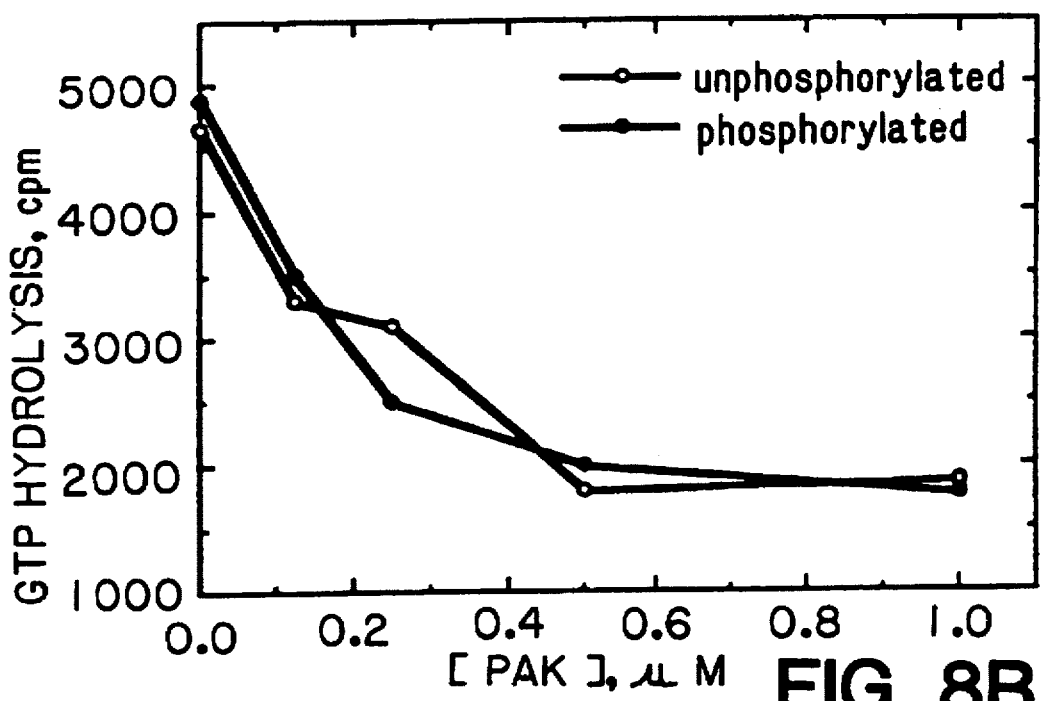

In contrast, when the catalytic domain of human p190 GAP (Settleman et al. 1992 disclosed rat p190) was included in the assay, hPAK65 exerted a significant inhibition of the GTP hydrolysis stimulated by p190. Increasing the concentration of hPAK65 to 5 fold greater than that of CDC42Hs resulted in blocking up to 40% of the GAP stimulated GTP hydrolysis (FIG. 8B). No differences in GAP stimulating GTPase were observed when phosphorylated hPAK 65 was compared to the unphosphorylated (FIG. 8B).

Rac1 and CDC42Hs share ~72% sequence identity and have distinct physiological roles. For instance, rac1 induces membrane ruffling (Ridley et al. 1992) and interacts with p67-phox to activate the NADPH oxidase (Dickmann et al. 1994), whereas CDC42Hs had no effect on NADPH oxidase activity or on the induction of membrane rufflings. In yeast, CDC42 is involved in bud formation (Johnson and Pringle 1990). The relative lower affinity of hPAK65 for rac1 compared to CDC42Hs may suggest that CDC42 Hs is the physiological activator of hPAK65. However, It is unlikely that hPAK65 activation by rac1 is an in vitro artifact, since in vitro activation of the NADPH oxidase specifically requires rac and not CDC42Hs. It is most probable that rho-like proteins have numerous effector domains, some of which may be shared among the various family members, whereas others may be unique to each member. Since the partial phosphopeptide map generated from activated hPAK65 either by rac or CDC42Hs were identical, this indicates that rac and CDC42Hs activate hPAK65 in the same fashion, namely, by the stimulation the autophosphorylation at the same sites. It will be very important to determine which agonist will link rac1 or CDC42Hs stimulation with hPAK65 activation in vivo. Such studies will determine which nucleotide exchange factor for rho-like proteins is implicated in this pathway. For example, Dbl was shown to have a nucleotide exchange activity on rho, CDC42Hs but not on rac1 (Hart et al. 1991). Thus it is possible that activation of Dbl may lead to CDC42Hs-dependent hPAK65 stimulation.

The homology of hPAK65 and rat brain PAK65 to the kinase domain of yeast STE20 suggests a role of rac/CDC42Hs and PAK proteins in the mitogen activiated protein ("MAP") kinase cascade in mammalian cells (Avruch et al 1994) which is involved in cell proliferation and transformation. STE20 was shown to be a target for the βγ subunits of the hetrotrimeric G protein in S. cerevisiae which link the pheromone response to a kinase cascade leading to transcription activation (Leberer et al. 1992, Errede and Levin 1993). Five protein kinases (STE20, STE11, STE7, FUS3 and KSS1) were implicated between the G proteins and the transcription factor STE12 (Errede and Levine 1993). STE7 has some homology to MAP kinase and FUS3 and KSS1 are yeast homologues of MAP kinase (Errede et al. 1993). In addition, genetic evidence demonstrates a functional association between a novel gene STE5 and STE20 (Leberer et al. 1993). Besides a limited homology to FAR1, STE5 has no specific known structural motif however operates within this kinase cascade and is most likely functions as an adaptor protein (Leberer et at. 1993, Errede and Levine 1993). The relatively high divergence between brain rat PAK65 and hPAK65 in their regulatory domains, suggest that these proteins may be controlled by different molecules. Thus, different mammalian STE5 homologues may serve as adaptor proteins to assemble distinct PAK like kinases with downstream kinases such as STE7 and STE11. Rac is believed involved in activating stress kinase pathways that can lead to, among other thigs, apoptosis. MEK kinase (MEKK), implicated in stress kinase pathways, may act downstream form hPAK65 since MEKK has homology to yeast STE11 which acts downstream from yeast STE20, a protein shown herein to have homology to hPAK65.

Figure 9:
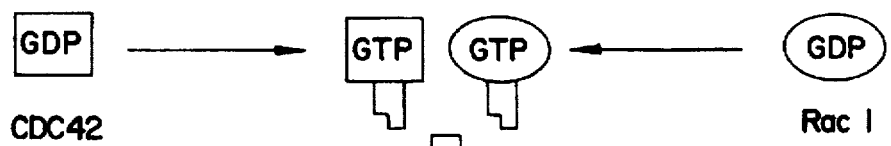
FIG. 9 presents a schematic of a model of the role of rac1/CDC42Hs in the activation of hPAK65 kinase. In step 1 rac1 or CDC42Hs exchange factors, which are stimualted by growth factors, stimulate the release of GDP from rac 1 or CDC42Hs and subsequently the binding of GTP to rac1 or CDC42Hs. In step 2 the activated rac1 or CDC42Hs binds to hPAK65. In step 3 rac1 or CDC42Hs induces the autophosphorylation of hPAK65 to activate hPAK65 serine kinase activity. In step 4 the intrinsic GTPase activity of rac1 or CDC42Hs hydrolyses the GTP to the inactive GDP state. In step 5 the GDP-bound form of rac1 or CDC42Hs dissociates from the active autophosphorylated hPAK65 kinase.
Figure 9:
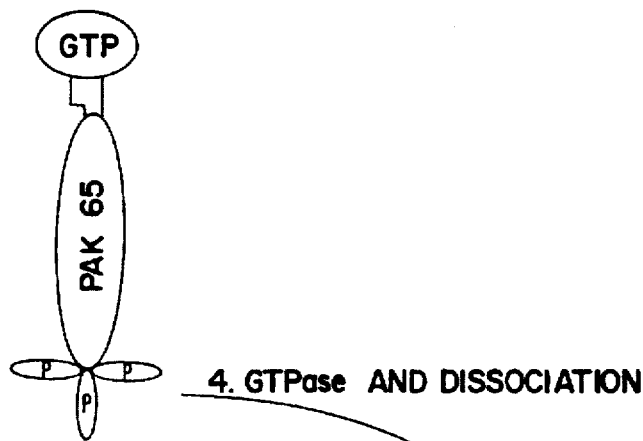
Figure 9:
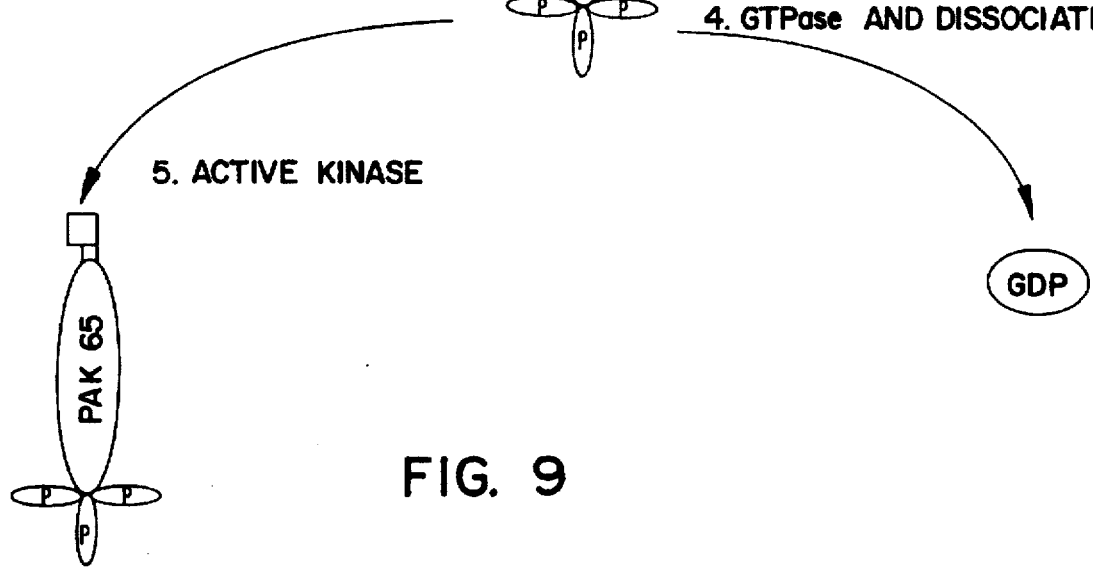

In summary the data presented herein are consistence with the model presented in FIG. 9. Upon exchange of the nucleotide from GDP to the active form GTP, rac1/CDC42Hs interact with hPAK65 and subsequently induce hPAK65 autophosphorylation. The GTP is hydrolyzed to GDP by the intrinsic GTPase activity of rac1/CDC42Hs. The inactive GDP-bound form of rac1 /CDC42Hs are released from the active hPAK65 kinase which subsequently phosphorylates as yet unidentified physiological substrate.

Example 13

Antibodies to hPAK65.

Antibody generated against a peptide derived from the kinase domain of hPAK65 was used to determine whether the other two effector proteins, p62 and p68, identified in neutrophil cytosol are related to hPAK65 proteins. No cross reactivity was observed using polyclonal sera.

Example 14

A Rac/CDC42 hPAK65 binding ELISA.

The following ELISA format assay provides one embodiment of a means to detect or measure the binding of p21 proteins to hPAK65 or fragments thereof, and thus provide one means to screen for agents that modulate this binding. A surface, eg. of a microtiter well, was coated with hPAK65 protein solution prepared by first adding 0.5 mM DTF to Dulbecco's phosphate buffered saline (containing Ca$^{2+}$ and Mg2+) followed by adding substantially purified GST-pakette fusion protein to a final concentration of 10 ug/ml (for 0.5 ug/well). After gentle mixing preferably by inversion, 50 ul of this GST-PAKette solution was placed into each well of a microtiter plate, e.g. Immulon plate, which was then covered with plate sealer and incubated overnite, preferably at 4° C. and preferably with rocking to evenly distribute the solution across the surface. Coated plates were typically useable for 4-5 days. Prior to use the plate was washed once with 200 ul of wash buffer: PBS containing Ca$^{2+}$ and Mg$^{2+}$ plus 0.1% tween-20. Non-specific binding sites were blocked by adding to each well 200 ul of PBS containing Ca$^{2+}$, Mg$^{2+}$ and 1% BSA, with incubation 4° C. for at least 2 hours, preferably with rocking, followed by two washes with 200 ul wash buffer each time.

Either recombinant tagged human rac1 or CDC42Hs were mixed at desired concentrations with 1 mM GDP/GTPγS and EDTA (at twice the MgCl$_2$ molar concentration in order to chelate Mg$^{2+}$) to a total of ~3× the volume of rac1/CDC42Hs added. The volume was adjusted with pre-bind buffer (50 mM Tris pH 8, 50 mM NaCl). The p21 protein solution was then incubated at 30° C. for 30 minutes. MgCl$_2$ was added to twice the EDTA molar concentration. Magnesium ion stimulates nucleotide binding to p21 proteins. EDTA chelates Mg$^{2+}$ to aid in nucleotide removal.

For binding, the above p21 protein solution was adjusted to volume with binding buffer (50 mM Tris pH 8, 50 mM NaCl, 50 mM MgCl$_2$, 1% NP-40 0.1% BSA). Binding was commenced by adding 50 ul of rac1/CDC42Hs solution to each well. To test an agent for its ability to inhibit or modulate binding, a test agent was added at 10 uM to the 50 ul solution (e.g., 5 μl agent +45 μl rac1/CDC42 GTPγS solution). Binding was allowed to proceed for 1 hour at 35° C. The wells were then washed three times with 200 ul wash buffer each time.

To detect hPAK65-bound rac1/CDC42Hs, an antibody-alkaline phosphatase conjugate ("Ab-AP") recognizing the appropriate tag was added to each well. Typically, antibody-AP conjugate was diluted 1:4000 into Ab dilution buffer (PBS containing Ca$^{2+}$ and Mg$^{2+}$, 0.1% Tween-20, 0.1% BSA) and then 50 ul Ab-AP solution was added to each well. After incubation for 1 hr at RT, each well was washed three times with 200 ul wash buffer. 100 ul of substrate for AP (stock: 1 tablet PNPP (Boeringher-Mannheim) in 100 mls H$_2$O) was added to each well followed by incubation at 10-20 minutes at 35° C. to develop color. The color was read at 405 nm when OD was about 1.0.

A candidate agent is one which significantly inhibits rac1 or CDC42Hs binding to GST-PAKette, and preferably has an IC$_{50}$ (concentration at which 50% of maximal inhibition occurs) in the range of less than 1 μM and more preferably less than 1 nM. Most preferably an agent will exhibit selectivity in inhibition of binding by not substantially inhibiting other p21 protein:protein kinase pairs, preferably with at least a two-fold, more preferably at least a three-fold, and even more preferably at least a ten-fold selectivity.

Example 15

Screening for Compounds that Inhibit hPAK65 Kinase Activity.

Compounds can be evaluated in an in vitro assay format for the ability to inhibit human PAK65 kinase activity for the substrate MBP. The general assay formats are as provided in the Examples above. Another assay can be adapted (MacDonald et al. (1993) Mol. Cell. Biol. 13: 6615) as follows: purified human PAK65 protein and purified MBP are combined in a reaction vessel (e.g., a microtiter plate well) under buffered aqueous conditions in the presence of γ-$^{33}$P-ATP and incubated at 32° C.; kinase catalyzed incorporation of $^{33}$P into protein is detected as radioactive counts retained on phosphocellulose paper after rinsing to remove unbound (i.e., non-protein) components, including γ-$^{33}$P-ATP. Test agents are included in parallel reactions and evaluated for their ability to inhibit hPAK65-dependent incorporation of sap into protein retained on phosphocellulose. In an alternate embodiment, γ-$^{32}$P-ATP can be used in place of γ-$^{33}$P-ATP. In a second alternate embodiment, a peptide, such as CQQFGFGRRASDDG may be used in place of MBP (Kolch et al. (1993) Nature 364: 249).

A candidate agent is one which significantly inhibits hPAK65 kinase activity, and preferably has an IC$_{50}$ (concentration at which 50% of maximal inhibition occurs) in the range of approximately 3×10$^{-8}$M. Most preferably an agent will exhibit selectivity in inhibition of hPAK65 by not substantially inhibiting protein kinase C (PKC) activity at concentrations up to 1×10$^{-5}$M. More preferably, an agent should neither significantly inhibit rasGAP nor rapGAP activity by 1×10$^{-5}$M agent under standard assay conditions for those activities.

Example 16

Inhibition of Human Tumor Growth in SCID Mouse.

To evaluate the ability of a candidate agent to inhibit human tumor growth, human tumor cells were injected into SCID mice (severe combined immunodeficiency) to form palpable tumor masses. The effects of an candidate agent in inhibiting tumor growth can be determined as follows. Approximately 1×10$^7$ cells of the CCL 221 cell line (ATCC, Rockville, Md.), a human ras-dependent colon adenocarcinoma cell line, is suspended in 100 μl DMEM and injected subcutaneously into SCID mice, such that two tumors per mouse are formed. SCID mice receive CCL 221 cells and the tumors are grown for 7 days without treatment; on the 7th day (Day 0) tumor maximal diameters and animal weights are recorded. On Day 0, the mean tumor size for the mice is determined. On Day 1 (eight days following tumor cell injection), treatment of the mice with candidate agent or vehicle alone was begun. One group of the mice (controls) were injected intraperitoneally with 0.2 ml of vehicle and a second group of mice received agent by intraperitoneal injection. Various doses of agent can be tested in separate groups of mice. On Day 7 and Day 14, animal weight and maximal tumor diameter is measured. Average maximal tumor size for each group on Day 0, Day 7, and Day 14 are compared Day 14, one high dose animal was followed for an additional to determined whether the agent produces a dose-dependent inhibition of tumor growth. Toxicity effects can be examined by tracking mice weight and by harvesting lungs, livers, and spleens of the animals for histologically staining.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide comprising a nucleic acid sequence having at least 95% identity to a nucleic acid sequence selected from the group consisting of:
   a) nucleotides 391 to 1908 of SEQ ID No. 1,
   b) nucleotides 535 to 729 of SEQ ID No. 1,
   c) nucleotides 1081 to 1848 of SEQ ID No. 1,
   d) nucleotides 391 to 1833 of SEQ ID No. 1, and
   e) nucleotides 391 to 1854 immediately followed by nucleotides 1864 to 1908 of
   SEQ ID No.1, without any intervening nucleic acid sequence therebetween.

2. The polynucleotide of claim 1, wherein said nucleic acid sequence has at least 99% identity to (a), (b), (c), (d), or (e).

3. The polynucleotide of claim 1, wherein said nucleic acid sequence has 100% identity to (a), (b), (c), (d), or (e).

4. The polynucleotide of claim 1, wherein said polynucleotide comprises nucleotides 391 to 1908 of SEQ ID No. 1.

5. The polynucleotide of claim 1, wherein said polynucleotide comprises nucleotides 535 to 729 of SEQ ID No. 1.

6. The polynucleotide of claim 1, wherein said polynucleotide comprises nucleotides 1081 to 1848 of SEQ ID No. 1.

7. The polynucleotide of claim 1, wherein said polynucleotide comprises nucleotides 391 to 1833 of SEQ ID No. 1.

8. The polyncleotide of claim 1, wherein said polynucleotide comprises nucleotides 391 to 1854 immediately followed by nucleotides 1864 to 1908 of SEQ ID No. 1, without any intervening nucleic acid sequence therebetween.

9. The polynucleotide of claim 1, further comprising a stop codon 3' of and in correct reading frame with respect to said nucleic acid sequence, wherein said polynucleotide encodes a polypeptide comprising an amino acid sequence selected from the group of:
   i) amino acid 1 to 506 of SEQ ID No. 2
   ii) amino acid 49 to 113 of SEQ ID No. 2
   iii) amino acid 231 to 481 of SEQ ID No. 2
   iv) amino acid 1 to 486 of SEQ ID No. 2
   v) SEQ ID No. 2, wherein amino acids 489 to 491 are absent.

10. The polynucleotide of claim 2, wherein said polynucleotide comprises a GAX nucleic acid sequence substitution for one or more of the nucleotide triplets 1528–1530, 1537–1539, 1540–1542, wherein X is selected from the group of nucleotides consisting of G, A, T, or C.

11. A vector comprising a polynucleotide of claim 1.

12. A host cell transformed with a polynucleotide of claim 1.

13. The host cell of claim 12, wherein said nucleic acid sequence is operably linked to an expression control sequence.

14. The host cell of claim 13, wherein said nucleic acid sequence is directly linked to an expression control sequence.

15. The host cell of claim 13, wherein said nucleic acid is constitutively expressed.

* * * * *